(12) United States Patent
Faucher et al.

(10) Patent No.: US 10,322,213 B2
(45) Date of Patent: Jun. 18, 2019

(54) COMPOSITIONS AND METHODS FOR ALTERING THE RATE OF HYDROLYSIS OF CURED OIL-BASED MATERIALS

(75) Inventors: Keith M. Faucher, Milford, NH (US); Theresa K. Albergo, Nashua, NH (US); Paul Martakos, Pelham, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 0 days.

(21) Appl. No.: 13/184,512

(22) Filed: Jul. 16, 2011

(65) Prior Publication Data
US 2012/0016038 A1 Jan. 19, 2012

Related U.S. Application Data

(60) Provisional application No. 61/365,125, filed on Jul. 16, 2010.

(51) Int. Cl.
| | | |
|---|---|---|
| *A61L 29/08* | (2006.01) | |
| *A61L 29/14* | (2006.01) | |
| *A61L 31/08* | (2006.01) | |
| *C08L 91/00* | (2006.01) | |
| *C09D 191/00* | (2006.01) | |

(52) U.S. Cl.
CPC ............ *A61L 31/08* (2013.01); *A61L 29/08* (2013.01); *A61L 29/148* (2013.01); *C09D 191/00* (2013.01); *A61L 2300/22* (2013.01); *A61L 2300/604* (2013.01)

(58) Field of Classification Search
CPC ... C09D 191/00; C08L 91/00; A61L 2300/22; A61L 2300/604; A61L 29/08; A61L 29/148; A61L 31/08
See application file for complete search history.

(56) References Cited

U.S. PATENT DOCUMENTS

| | | |
|---|---|---|
| 1,948,959 A | 2/1934 | Croce |
| 2,368,306 A | 1/1945 | Kiefer et al. |
| 2,403,458 A | 7/1946 | Ransom |
| 2,735,814 A | 2/1956 | Hodson et al. |
| 2,986,540 A | 5/1961 | Posnansky |
| 3,328,259 A | 6/1967 | Anderson |
| 3,464,413 A | 9/1969 | Goldfarb et al. |
| 3,556,294 A | 1/1971 | Walck et al. |
| 3,567,820 A | 3/1971 | Sperti |
| 3,803,109 A | 4/1974 | Nemoto et al. |
| 3,967,728 A | 7/1976 | Gordon et al. |
| 4,308,120 A | 12/1981 | Pennewiss et al. |
| 4,323,547 A | 4/1982 | Knust et al. |
| 4,447,418 A | 5/1984 | Maddoux |
| 4,557,925 A | 12/1985 | Lindahl et al. |
| 4,664,114 A | 5/1987 | Ghodstain |
| 4,813,210 A | 3/1989 | Masuda et al. |
| 4,814,329 A | 3/1989 | Harsanyi et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,947,840 A | 8/1990 | Yannas et al. |
| 4,952,419 A | 8/1990 | de Leon |
| 4,968,302 A | 11/1990 | Schluter et al. |
| 5,017,229 A | 5/1991 | Burns et al. |
| 5,061,281 A | 10/1991 | Mares et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,179,174 A | 1/1993 | Elton |
| 5,202,310 A | 4/1993 | Levy et al. |
| 5,176,956 A | 5/1993 | Jevne et al. |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 6/1995 | Bochow et al. |
| 5,447,940 A | 9/1995 | Harvey et al. |
| 5,464,650 A | 11/1995 | Berg et al. |
| 5,480,436 A | 1/1996 | Bakker et al. |
| 5,480,653 A | 1/1996 | Aguadish et al. |
| 5,502,077 A * | 3/1996 | Breivik .................. A61K 31/20 514/549 |
| 5,509,899 A | 4/1996 | Fan et al. |
| 5,547,677 A | 8/1996 | Wright |
| 5,549,901 A | 8/1996 | Wright |
| 5,579,149 A | 11/1996 | Moret et al. |
| 5,580,923 A | 12/1996 | Yeung et al. |
| 5,589,508 A | 12/1996 | Schlotzer et al. |

(Continued)

FOREIGN PATENT DOCUMENTS

| | | |
|---|---|---|
| EP | 0471566 | 2/1992 |
| EP | 0610731 | 8/1994 |

(Continued)

OTHER PUBLICATIONS

Lipids, Chapter 19, (Mar. 16, 2002), pp. 1-12.*

(Continued)

*Primary Examiner* — Mark V Stevens
(74) *Attorney, Agent, or Firm* — Wesley Scott Ashton

(57) ABSTRACT

Disclosed herein is the correlation of chemical properties of oils with the physical properties of a resulting cured oil composition. Also disclosed are biocompatible materials and coatings for medical devices prepared using enriched oils and methods for enhancing or modifying the physical and chemical characteristics of cured oils by enriching such oils with fatty acid alkyl esters. Methods of tailoring the properties of biocompatible materials and coatings to deliver one or more therapeutic agents are also provided.

30 Claims, 11 Drawing Sheets

(56) References Cited

U.S. PATENT DOCUMENTS

| | | |
|---|---|---|
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,629,021 A | 5/1997 | Wright |
| 5,634,931 A | 6/1997 | Kugel |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,731,346 A | 3/1998 | Egberg et al. |
| 5,736,152 A | 4/1998 | Dunn |
| 5,747,533 A | 5/1998 | Egberg et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,048,725 A | 4/2000 | Shimada et al. |
| 6,056,970 A | 5/2000 | Greenawalt et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,366 B1 | 6/2001 | Popplewell et al. |
| 6,245,811 B1 | 6/2001 | Harrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,696,583 B2 | 2/2004 | Koncar et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 7,854,958 B2 | 12/2010 | Kramer |
| 7,947,015 B2 | 5/2011 | Herweck et al. |
| 8,124,127 B2 | 2/2012 | Faucher et al. |
| 8,263,102 B2 | 9/2012 | Labrecque et al. |
| 8,308,684 B2 | 11/2012 | Herweck et al. |
| 8,312,836 B2 | 11/2012 | Corbeil et al. |
| 8,367,099 B2 | 2/2013 | Herweck et al. |
| 8,501,229 B2 | 8/2013 | Faucher et al. |
| 8,722,077 B2 | 5/2014 | Labrecque et al. |
| 9,000,040 B2 | 4/2015 | Faucher et al. |
| 9,012,506 B2 | 4/2015 | Faucher et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1 | 1/2003 | Yang |

(56) References Cited

U.S. PATENT DOCUMENTS

| | | |
|---|---|---|
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 6/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0131755 A1 | 7/2004 | Along et al. |
| 2004/0133275 A1 | 7/2004 | Mansmann |
| 2004/0137066 A1 | 7/2004 | Jayaraman |
| 2004/0137179 A1 | 7/2004 | Shojiro et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Car Enter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0030669 A1* | 2/2006 | Taton ............... A61L 31/10 525/242 |
| 2006/0036311 A1 | 2/2006 | Nakayama et al. |
| 2006/0051544 A1 | 3/2006 | Goldmann |
| 2006/0058881 A1 | 3/2006 | Trieu |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 12/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1* | 7/2009 | Faucher ............... A61K 31/225 514/183 |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 1952807 A1 | 8/2008 |
| EP | 07867319 | 8/2009 |
| EP | 1402906 | 6/2011 |
| KR | 20080025986 | 3/2008 |
| WO | WO 1986/000912 | 7/1984 |

(56) References Cited

FOREIGN PATENT DOCUMENTS

| | | |
|---|---|---|
| WO | WO 1990/001969 | 3/1990 |
| WO | 90/008544 A1 | 8/1990 |
| WO | WO 1995/026715 | 10/1995 |
| WO | WO 1997/002042 | 1/1997 |
| WO | WO 1997/009367 | 3/1997 |
| WO | WO 1997/013528 | 4/1997 |
| WO | WO 1998/030206 | 7/1998 |
| WO | 98/46287 A2 | 10/1998 |
| WO | WO 1998/054275 | 12/1998 |
| WO | WO 1999/025336 | 5/1999 |
| WO | WO 2000/40278 | 7/2000 |
| WO | WO 2000/62830 | 10/2000 |
| WO | WO 2001/024866 | 4/2001 |
| WO | WO 2001/026585 | 4/2001 |
| WO | WO 2001/037808 | 5/2001 |
| WO | WO 2001/060586 | 8/2001 |
| WO | WO 2001/066036 | 9/2001 |
| WO | WO 2001/076649 | 10/2001 |
| WO | WO 2002/049535 | 6/2002 |
| WO | WO 2002/100455 | 12/2002 |
| WO | WO 2003/000308 | 1/2003 |
| WO | WO 2003/015748 | 2/2003 |
| WO | WO 2003/028622 | 4/2003 |
| WO | WO 2003/037397 | 5/2003 |
| WO | WO 2003/037398 | 5/2003 |
| WO | WO 2003/039612 | 5/2003 |
| WO | WO 2003/041756 | 5/2003 |
| WO | WO 2003/070125 | 8/2003 |
| WO | WO 2003/092741 | 11/2003 |
| WO | WO 2003/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | 20040101010 A1 | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | 2008/010788 A2 | 1/2008 |
| WO | 2008/016664 A2 | 2/2008 |
| WO | WO 2008/057328 | 5/2008 |
| WO | 2010/042134 A1 | 4/2010 |
| WO | 2010/042241 A1 | 4/2010 |
| WO | WO 2012/009707 | 1/2012 |

OTHER PUBLICATIONS

Jorge, N., Grasas y Aceites, Vo. 48, Fasc. 1, (1997), pp. 17-24.*
Saghir et al (American Journal of Physiology, Gastrointestinal and Liver Physiology, 1997, vol. 273, pp. G184-G190) (Year: 1997).*
Autosuture, "ParietexTM Composite OS Series Mesh," retrieved online at http://www.autosuture.com/AutoSuture/pagebuilder.aspx?topicID=135734&breadcrumbs=135601:0 (2007).
Binder et al., "Chromatographic Analysis of Seed Oils Fatty Acid nomposition of Castor Oil," The Journal of the American Oil Chemists' Society, vol. 39:513-517 (1962).
Camurus, "In our endeavors to create the unique, we start with the best. Your product."
Redman, L.V. et al., "The drying rate of raw paint oils—a comparison," The Journal of Industrial and Engineering Chemistry, vol. 5: 630-636 (1913).
De Scheerder, Ivan K., et al. "Biocompatibility of polymer-coated oversized metallic stents implanted in normal porcine coronary arteries," Atherosclerosis, vol. 114:105-114.

Drummond, Calum J., et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei, et al, "Physiological Transport Forces Govern Drug Distribution for Stent-Based Delivery," Circulation, vol. 104:600-605 (2001).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin, et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Salu, Koen J., et al, "Addition of cytochalasin D to a biocompatible oil stent coating inhibits intimal hyperplasia in a porcine coronary model," Coronary Artery Disease, vol. 14(8):545-555 (2003).
Scheller, Bruno, et al, "Addition of Paclitaxel to Contrast Media Prevents Restenosis After Coronary Stent Implantation," Journal of the American College of Cardiology, vol. 42(8):1415-1420 (2003).
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Ogunniyi, D.S., "Castor oil: A vital industrial raw material," Biosource Technology, vol. 97: 1086-1091 (2006).
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Timir-Balizsy et al., "Chemical Principals of Textile Conservation," Oxford: Elsevier Science Ltd., 1998:117-119.
A paper entitled "Evaluation of the Biocompatibility and Drug Delivery Capabilities of Biological Oil Based Stent Coatings" by Shengqio Li of the Katholieke Universiteit Leuven.
"Polymerization" Merriam-Webster Online Dictionary, retrieved from <www.merriam-webster.com> on Dec. 13, 2009; Merriam-Webster's Inc. 2009; pp. 1.
Shahidi, Fereidoon ed.; "Bailey's Industrial Oil and Fats Products" 2005; John Wiley and Sons; vol. 5, Edible Oil and Fat Products: Processing Technologies, pp. 1-15.
Ahuja et al. Journal of Indian Pediatric Surgery 2002 7:15-20.
Jonasson, Lena et al., "Cyclosporon A inhibits smooth muscle proliferation in the vascular response to injury," Proc. Natl. Acad. Sci. USA, vol. 85: 2303-2306 (1988).
Wikipedia, "Sirolimus," pp. 1-13, available online at http://en.wikipedia.org/wiki/Sirolimus, date accessed May 11, 2011.
CECW-EE, "Ch. 4: Coating Types and Characteristics," Engineering and Design—Painting: New Construction and Maintenance, pp. 4-1 to 4-24 (1995).
Rutkow, Ira M. et al., "'Tension-free' inguinal herniorrhaphy: A preliminary report on the 'mesh plug' technique," Surgery, vol. 114:3-8 (1993).
Websters Dictionary Online, Accessed on Feb. 13, 2009, entry for "polymer" p. 1 of 1.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.

(56) References Cited

OTHER PUBLICATIONS

International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
International Search Report for International Application No. PCT/US05/34941, dated May 4, 2006.
Supplementary European Search Report for Application No. EP 08877338.7, dated Aug. 16, 2012.
Supplementary European Search Report for Application No. EP09819594.4, dated Aug. 14, 2012.
International Search Report for PCT/US2011/44292, dated Dec. 6, 2011.
Non-final Office Action for U.S. Appl. No. 11/236,908, dated Mar. 25, 2006.
Final Office Action for U.S. Appl. No. 11/236,908, dated May 17, 2011.
Non-final Office Action for U.S. Appl. No. 11/236,908, dated Aug. 24, 2009.
Non-final Office Action for U.S. Appl. No. 11/236,977, dated Aug. 3, 2009.
Final Office Action for U.S. Appl. No. 11/237,263, dated Jul. 7, 2010.
Non-final Office Action for U.S. Appl. No. 11/237,263, dated Oct. 7, 2009.
Final Office Action for U.S. Appl. No. 11/237,264, dated Jun. 2, 2010.
Non-final Office Action for U.S. Appl. No. 11/237,264, dated Oct. 5, 2009.
Final Office Action for U.S. Appl. No. 11/701,799, dated Nov. 23, 2010.
Non-final Office Action for U.S. Appl. No. 11/237,420, dated Mar. 5, 2009.
Final Office Action for U.S. Appl. No. 11/237,420, dated Nov. 4, 2009.
Non-final Office Action for U.S. Appl. No. 11/237,420, dated Dec. 6, 2010.
Non-final Office Action for U.S. Appl. No. 11/238,532, dated Mar. 30, 2009.
Final Office Action for U.S. Appl. No. 11/238,532, dated Sep. 9, 2009.
Final Office Action for U.S. Appl. No. 11/238,554, dated May 12, 2010.
Non-final Office Action for U.S. Appl. No. 11/238,554, dated Oct. 9, 2009.
Final Office Action for U.S. Appl. No. 11/238,554, dated May 1, 2009.
Non-final Office Action for U.S. Appl. No. 11/238,554, dated Jul. 25, 2008.
Non-final Office Action for U.S. Appl. No. 11/238,564, dated Apr. 16, 2008.
Final Office Action for U.S. Appl. No. 11/238,564, dated Aug. 6, 2009.
Non-final Office Action for U.S. Appl. No. 11/239,555, dated Mar. 30, 2009.
Non-final Office Action for U.S. Appl. No. 11/525,328, dated Apr. 30, 2007.
Non-final Office Action for U.S. Appl. No. 11/525,390, dated Jul. 14, 2010.
Final Office Action for U.S. Appl. No. 11/525,390, dated Feb. 21, 2011.
Final Office Action for U.S. Appl. No. 11/582,135, dated May 12, 2011.
Non-final Office Action for U.S. Appl. No. 11/582,135, dated Nov. 9, 2010.
Non-final Office Action for U.S. Appl. No. 11/582,135, dated Jan. 6, 2010.
Non-final Office Action for U.S. Appl. No. 11/582,135, dated May 12, 2009.
Non-final Office Action for U.S. Appl. No. 11/701,799, dated Apr. 12, 2010.
Non-final Office Action for U.S. Appl. No. 11/978,840, dated Dec. 3, 2010.
Non-final Office Action for U.S. Appl. No. 11/980,155, dated Mar. 24, 2011.
Non-final Office Action for U.S. Appl. No. 12/075,223, dated Dec. 8, 2010.
Non-final Office Action for U.S. Appl. No. 12/325,546, dated Feb. 25, 2010.
Final Office Action for U.S. Appl. No. 12/325,546, dated Aug. 31, 2010.
Non-final Office Action for U.S. Appl. No. 12/364,763, dated Dec. 11, 2009.
Final Office Action for U.S. Appl. No. 12/364,763, dated Sep. 21, 2010.
Interview summary for U.S. Appl. No. 11/236,908 dated May 5, 2009.
Interview summary for U.S. Appl. No. 11/236,908 dated Dec. 2, 2010.
Interview summary for U.S. Appl. No. 11/237,420 dated May 5, 2009.
Interview summary for U.S. Appl. No. 11/582,135 dated Dec. 7, 2010.
Interview summary for U.S. Appl. No. 12/325,546 dated Dec. 2, 2010.
Interview summary for U.S. Appl. No. 12/364,763 dated Dec. 2, 2010.
Final Office Action for U.S. Appl. No. 11/237,420, dated Jul. 13, 2011.
Final Office Action for U.S. Appl. No. 11/978,840, dated Jun. 22, 2011.
Final Office Action for U.S. Appl. No. 12/075,223, dated Aug. 11, 2011.

(56) References Cited

OTHER PUBLICATIONS

Non-final Office Action for U.S. Appl. No. 11/525,390, dated Jul. 11, 2011.
Non-Final Office Action for U.S. Appl. No. 11/701,799, dated Aug. 17, 2011.
Non-Final Office Action for U.S. Appl. No. 11/582,135, dated Oct. 14, 2011.
Final Office Action for U.S. Appl. No. 11/980,155, dated Oct. 21, 2011.
Non-Final Office Action for U.S. Appl. No. 11/236,908, dated Dec. 2, 2011.
Non-Final Office Action for U.S Appl. No. 12/182,261, dated Dec. 21, 2011.
Non-Final Office Action for U.S. Appl. No. 12/401,243, dated Jan. 5, 2012.
Notice of Allowance for U.S. Appl. No. 11/582,135, dated Jan. 9, 2012.
Non-Final Office Action for U.S. Appl. No. 12/182,165, dated Jan. 5, 2012.
Final Office Action for U.S. Appl. No. 11/701,799, dated Feb. 13, 2012.
Non-Final Office Action for U.S. Appl. No. 12/581,582, dated Mar. 14, 2012.
Final Office Action for U.S. Appl. No. 12/182,165, dated Apr. 6, 2012.
Final Office Action for U.S. Appl. No. 12/182,261 dated Apr. 30, 2012.
Notice of Allowance for U.S. Appl. No. 11/236,908, dated May 11, 2012.
Final Office Action for U.S. Appl. No. 12/401,243, dated Jun. 11, 2012.
Notice of Allowance for U.S. Appl. No. 12/182,261, dated Jul. 23, 2012.
Advisory Action for U.S. Appl. No. 12/401,243, dated Aug. 27, 2012.
Final Office Action for U.S. Appl. No. 12/581,582 dated Aug. 29, 2012.
Notice of Allowance for U.S. Appl. No. 11/525,390, dated Oct. 4, 2012.
Final Office Action for U.S. Appl. No. 11/236,943, dated Dec. 23, 2009.
Non-Final Office Action for U.S. Appl. No. 11/236,943, dated Mar. 5, 2009.
Advisory Action for U.S. Appl. No. 12/581,582, dated Nov. 14, 2012.
Non-Final Office Action for U.S. Appl. No. 13/404,487, dated Dec. 20, 2012.
Notice of Allowance for U.S. Appl. No. 11/525,390, dated Nov. 20, 2012.
Notice of Allowance for U.S. Appl. No. 11/525,390, dated Nov. 30, 2012.
Ackman, R.G., "Fish Oils", *Bailey's Industrial Oil and Fat Products*, 6th Edition, 279-317 (2005).
Andes, et al. "Antiproliferative Strategies for the Treatment of Vascular Proliferative Disease", *Current Vascular Pharmacology*, 1)1): 85-98 (2003).
Winter, et al., "Physical and Chemical Gelation" *Encyclopedia of Materials—Science and Technology*, vols. 1-11: 6691-6999 (2001).
Non-Final Office Action for U.S. Appl. No. 11/978,840, dated Feb. 19, 2013.
Non-Final Office Action for U.S. Appl. No. 13/682,991, dated Mar. 18, 2013.
Notice of Allowance for U.S. Appl. No. 13/404,487, dated Apr. 2, 2013.
Non-Final Office Action for U.S. Appl. No. 13/593,656, dated Jul. 15, 2013.
Notice of Allowance for U.S. Appl. No. 13/682,991, dated Aug. 1, 2013.
Notice of Allowance for U.S. Appl. No. 11/978,840, dated Aug. 6, 2013.

Lipids, Chapter 19, pp. 1-12 (2002).
Jorge, N., "Grasas y Aceites", 48(1): 17-24, (1997).
Supplementary European Search Report for EP12004057, dated Apr. 10, 2013.
International Search Report for International Application PCT/US2013/044653, dated Sep. 4, 2013.
Non-Final Office Action for U.S. Appl. No. 11/236,943, dated Apr. 22, 2013.
Non-Final Office Action for U.S. Appl. No. 11/237,264, dated Jul. 3, 2013.
Mallegol, "Long-Term Behavior of Oil-Based Varnishes and Paints Photo-and Thermooxidation of Cured Linseed Oil", *Journal of the American Oil Chemists' Society*, 77:257-263 (2000).
Non-Final Office Action for U.S. Appl. No. 11/237,420, dated Nov. 12, 2013.
Non-Final Office Action for U.S. Appl. No. 12/075,223, dated Nov. 12, 2013.
Non-Final Office Action for U.S. Appl. No. 11/980,155, dated Nov. 12, 2013.
Final Office Action for U.S. Appl. No. 11/236,943, dated Dec. 4, 2013.
Final Office Action for U.S. Appl. No. 11/237,264, dated Dec. 17, 2013.
Notice of Allowance for U.S. Appl. No. 13/593,656, dated Jan. 24, 2014.
Notice of Allowance for U.S. Appl. No. 11/237,264, dated Mar. 27, 2014.
Notice of Allowance for U.S. Appl. No. 11/237,263, dated Mar. 27, 2014.
Supplementary European Search Report for Application No. EP 10825447, dated Mar. 31, 2014.
Non Final Office Action for U.S. Appl. No. 12/325,546, dated Apr. 22, 2014.
Non Final Office Action for U.S. Appl. No. 12/364,763, dated Apr. 23, 2014.
Non Final Office Action for U.S. Appl. No. 12/401,243, dated May 8, 2014.
Non Final Office Action for U.S. Appl. No. 12/581,582, dated May 29, 2014.
Uchida, et al., "Swelling Process and Order-Disorder Transition of Hydrogel Containing Hydrophobic Ionizable Groups", *Macromolecules*, 28, 4583-4586 1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1299 (1997).
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.
Wikipedia, Sunflower oil, https://en.wikipedia.org/wiki/Sunflower_oil, accessed Jul. 23, 2015 in related U.S. Appl. No. 14/252,671, pp. 1-7.
Esoteric Oils, Peppermint essential oil information, http://www.essentialoils.co.za/essential-oils/peppermint.htm, accessed Jul. 23, 2015 in related U.S. Appl. No. 14/252,671, pp. 1-7.
Orthomolecular, Fish Oil, Jun. 29, 2004, http://orthomolecular.org/nutrients/fishoil.html, accessed Jul. 22, 2015 in related U.S. Appl. No. 14/252,671, p. 1.
Final Office Action for U.S. Appl. No. 13/843,068, dated Apr. 23, 2015.
Wicks et al. Organic Coatings:Science and Technology 1999 New York:Wiley Interscience, pp. 258-267.
Mills et al. Oils and Fats. "The Organic Chemistry of Museum Objects" London:Buttersworth and Co. 1987, pp. 26-40.

(56) References Cited

OTHER PUBLICATIONS

Erhardt Paints Based on Drying Oil Media. Painted Wood: History & Conservation. Ed. Berland Singapore: The J. Paul Getty Trust 1998. pp. 17-32.
Wexler et al. Chemical Reviews 1964, vol. 64, No. 6, pp. 591-611.
Polymer—The Chambers 21st Century Dictionary M. Robinson and G. Davidson (Eds.), London, United Kingdom: Chambers Harrap. Retrieved from http://search.credoreference.com/contentientry/chambdict!polymer/O.
Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/O.
Falagas et al. European Society of Clinical Microbiology and Infection Diseases, 2005, vol. 11, pp. 3-8.
Bimbo, INFORM 1998, vol. 9, No. 5, pp. 473-483.
Oxford Reference, A Dictionary of Chemistry, 6th edition, John Daintith, 2008, 3 pages.
H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?d=9&sub=20&cont=522 (downloaded Nov. 10, 2015).
Refined soybean oil not an allergen, say food scientists, Food navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.

Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hultin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:iessionid=33N2RBQDV0DZKCQPCCEGU3AKB2IIWTT1 (2006).
Orthovisc, "What is Orthovisc®?" retrieved online at http://www.orthovisc.com/xhtmlbgdisplay.jhtml?itemname=about_orthovisc (2005).
Orthovisc, "Your Knees and Osteoarthritis", retrieved online at http://www.orthovisc.com/xhtmlbgdisplay.jhtml?itemname=understanding_knee_oa (2003).
Orthovisc, "What to expect from your treatment," retrieved online at http://www.orthovisc.com/xhtmlbgdisplay.jhtml?itemname=what_to_expect (2007).
Orthovisc, "Tools and Resources for Managing Your Osteoarthritis", retrieved online at http://www.orthovisc.com/xhtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).

(56) References Cited

OTHER PUBLICATIONS

Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (! 387).
Hortolam, Juliane G., et al., "Connective tissue diseases following silicone breast implantation: where do we stand?", Clinics, 2013, vol. 3, p. 281.
Lidar, M. et al., "Silicone and sclerodema revisited", Lupus, 2012, vol. 21, pp. 121-127.
"Lead", Article by Centers for Disease Control and Prevention (CDC), Nov. 2009, 2 pages.
"Cure" in Academic Press Dictionary of Science and Technology, 1992.
European Extended Search Report dated Jan. 18, 2016, issued for corresponding EP Patent Application No. 11807612.4, 7 pages.
Triglycerides, at https://www.lipid.org/sites/default/files/triglycerides.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015)).
Swanson, Danielle, et al., Omega-3 Fatty Acids EPA and DHA: Health Benefits Throughout Life, 3 Advances in Nutrition 1-7 (American Society for Nutrition 2012).
Fats & Oils (2008) at http://scifun.chem.wisc.edu/chemweek/pdf/fats&oils.pdf (downloaded Sep. 24, 2015).
John McMurray, Organic Chemistry, third edition, 1992, pp. 45-48.
9.1 Terminology for Vegetable Oils and Animal Fats, at http://www.e-education.psu.edu/egee439/node/683 (downloaded Sep. 13, 2017), pp. 1-8.
Sunflower Oil, at https://en.wikipedia.org/wiki/Sunflower_oil (downloaded Sep. 19, 2017), pp. 1-8.
Fatty Acid Composition of Marine Oils by GLC, AOCS Official Method Ce 1b-89 (2009), pp. 1-7.
Preparation of Methyl Esters of Fatty Acids, AOCS Official Method Ce 2-66 (2009), pp. 1-2.
U.S. Office Action dated Sep. 19, 2018 for related U.S. Appl. No. 15/817,018, 47 pages.

\* cited by examiner

COMPOSITIONS AND METHODS FOR ALTERING THE RATE OF HYDROLYSIS OF CURED OIL-BASED MATERIALS

RELATED APPLICATIONS

This application claims priority to, and the benefit of, U.S. Application No. 61/365,125, filed on Jul. 16, 2010. The entire teachings of the above application(s) are incorporated herein by reference.

The disclosures of co-pending U.S. Publication Nos. 2006/0078586 to Ferraro et al., published Apr. 13, 2006, entitled "Barrier layer", 2006/0067983 to Swanick et al., published Mar. 30, 2006, entitled "Stand-alone film and methods for making the same", 2006/0067974 to Labrecque et al., published Mar. 30, 2006, entitled "Drug delivery coating for use with a stent", 2007/0202149 to Faucher et al., published Aug. 30, 2007, entitled "Hydrophobic cross-linked gels for bioabsorbable drug carrier coatings", 2009/0181937 to Faucher et al., published Jul. 16, 2009, entitled "Cross-linked Fatty Acid-Based Biomaterials" and 2009/0208552 to Faucher et al., published Aug. 20, 2009, entitled "Cross-linked Fatty Acid-Based Biomaterials" which relate to oil coatings and materials used as stand-alone films and as medical device coatings are incorporated herein by reference in their entirety.

BACKGROUND OF THE INVENTION

The availability of oils that may be cured and used to develop biocompatible materials (e.g., for use as drug delivery vehicles, stand-alone films, or as coatings on medical devices) remains limited. Depending on the intended application of the cured oil composition (e.g., as a coating on a substrate such as a medical device) the physical properties of the oil used to prepare such cured oil composition may render it unsuitable for its intended application.

Cured oils that have been successfully developed have relied predominantly on fish oil triglyceride esters as the starting oil composition. In addition to fish oil, there are numerous other oils that may have potential applicability in the development of biocompatible products such as cured coatings and materials, however many of these oils may not be suitable for specific applications because of their inherent physical and chemical properties. For example, some oils may not effectively form solid gels, materials or coatings upon exposure to appropriate curing conditions. Similarly, some oils that are capable of forming solid coatings, materials or gels may not readily dissolve or hydrolyze upon exposure to appropriate conditions (e.g., in aqueous fluids), thereby making their use unsuitable for certain applications (e.g., as a vehicle or matrix with which to deliver a therapeutic agent to an intended site of action).

Novel methods and compositions for tailoring or otherwise altering the physical characteristics of cured oils are needed. Particularly needed are means of tailoring the properties of cured oils (e.g., viscosity and hydrophilicity) such that they may be rendered suitable for use, for example, as gels, materials and/or coatings useful for delivering one or more therapeutic agents. Also needed are methods and compositions useful for altering the polarity and/or hydrolysis rate of a cured oil coating, material or gel as a means to control the rate of release of a therapeutic agent to a target organ.

SUMMARY OF THE INVENTION

The present invention provides novel methods and compositions that may be used to tailor the physical characteristics of cured oils, such as marine and plant oils, to render such cured oils suitable for use, for example, as a biocompatible material for use as or with a medical device or as a coating capable of eluting one or more therapeutic agents. In certain embodiments, the methods and compositions disclosed herein identify and exploit the chemical properties of oils, both in native and synthetic form, that influence their ability to form both hydrolyzable and non-hydrolyzable cured oil based products or materials (e.g., a biocompatible material or coating, including a gel, or films, particles, or other structures or formations). In other embodiments, the methods and compositions disclosed herein relate to modifying and/or enhancing the physical and/or chemical characteristics of the oils that are used to prepare such cured oil materials or coatings, and include modifications or enhancements made to enhance the probability that such oils will form a biocompatible cured oil material or coating. Also disclosed are correlations to altering starting oil compositions (e.g., by blending of different oils) and the resulting cured coating prepared therefrom and methods of modifying or enriching such oil compositions such that the characteristics of the cured coatings prepared therefrom are modified. The methods and compositions of the present invention expand the population of oils that upon curing may be used as a stand-alone film, particle, as a coating on medical devices, or the like, and thereby enhance the ability to customize oil coatings based upon desired physical characteristics (e.g., release of a therapeutic agent, resorption kinetics and/or rate of coating hydrolysis in vivo).

Disclosed herein are cured oil based products or materials capable of use on or within a medical device and which comprise one or more cross-linked fatty acids, wherein the oils used to prepared such cross-linked fatty acids have been structurally modified from their native form to be enriched with one or more fatty acid alkyl esters (e.g., lower alkyl esters of fatty acids) prior to curing. In one embodiment, the esterified fatty acid used to enrich the oil is a lower alkyl ester of a fatty acid (e.g., an ethyl ester of eicosapentaenoic acid (EPA) and/or docosahexaenoic acid (DHA)). Contemplated lower alkyls esters may be selected from the group consisting of linear and branched $C_1$-$C_6$ alkyls and include, for example, methyl, ethyl, propyl, butyl, pentyl, hexyl (e.g., in both linear and branched forms) and combinations thereof. Preferred fatty acid alkyl esters include, for example, the ethyl esters of eicosapentaenoic acid (EPA), ethyl esters of docosahexaenoic acid (DHA) and combinations thereof.

In certain embodiments, the inventions relate to cured coatings (e.g., coatings that may be disposed or otherwise applied onto a medical device) or materials that are prepared using an enriched oil composition (e.g., blended oil compositions). Such enriched oil compositions may generally comprise one or more oils (e.g., a native oil such as fish oil triglycerides or a plant oil such as flaxseed oil) to which is added one or more fatty acid alkyl esters (e.g., lower alkyl esters of eicosapentaenoic acid (EPA) and/or docosahexaenoic acid (DHA)). In some embodiments, the enriched oil comprises flaxseed oil and ethyl esters of eicosapentaenoic acid (EPA) and/or docosahexaenoic acid (DHA). In other embodiments, the enriched oil comprises native fish oil triglycerides and ethyl esters of eicosapentaenoic acid (EPA) and/or docosahexaenoic acid (DHA). The enriched oil compositions used to form such cured oil coatings and materials may comprise between about 1% to about 99% fatty acid alkyl esters (e.g., about 10-90% or about 25-75% fatty acid alkyl esters).

In certain embodiments, the enriched oils may be prepared by blending or otherwise combining one or more marine or plant oils with a second oil (e.g., fish oil ethyl esters) to form a blended oil compositions. In certain embodiments, the enriched oils may be prepared by blending or otherwise combining one or more marine or plant oils with a second, third or fourth oil. Suitable plant oils may include, for example, flaxseed oil, grapeseed oil, safflower oil, soybean oil, corn oil, echium oil, hempseed oil, walnut oil, olive oil and combinations thereof.

The coatings disclosed herein may be prepared from oils or enriched oils comprising at least about 50% polyunsaturated fatty acids. For example, the coatings may be prepared by curing (e.g., thermally curing) an enriched oil comprising at least about 60-65% polyunsaturated fatty acids (e.g., at least about 60-65% EPA and/or DHA).

In certain embodiments, the cured coatings and materials disclosed herein are hydrolyzable. Where such cured coatings are applied onto a substrate such as a medical device (e.g., a surgical mesh, a graft, a catheter balloon, a stand-alone film or a stent) they may be hydrolyzable in vivo. Disclosed are cured coatings and materials that undergo complete hydrolysis in a 0.1M NaOH solution in less than about 60 minutes at 37° C. (e.g., in about 30-45 minutes). Preferably, such cured coatings completely hydrolyze in vivo into substantially non-inflammatory compounds (e.g., free fatty acids, monoglycerides, diglycerides and glycerol). Also disclosed are cured coatings and materials that are porous or that otherwise comprise one or more voids.

In certain embodiments, the cured coatings and materials disclosed herein are non-hydrolyzable. Where such cured coatings are applied onto a substrate such as a medical device (e.g., a surgical mesh, a graft, a catheter balloon, a stand-alone film or a stent) or used to form a stand alone material they may not be hydrolyzable or absorbable in vivo, however, they may still maintain low to substantially non-inflammatory properties.

The coatings disclosed herein may be prepared such that they are hydrophilic in nature. For example, such coatings may be characterized as having a contact angle of less than about 90° (e.g., a contact angle less than 87.5°, 85°, 80°, 75°, 70°, 65°, 60°, 55°, 50°, 45°, or less). In other embodiments, the coatings described herein are characterized as having one or more polar functional groups (e.g., hydroxyl functional groups, as indicated by an infrared absorption spectrum having a peak absorbing at approximately 3300-3600 $cm^{-1}$). The presence of such polar groups render such coatings more hydrophilic and thereby increase the likelihood that such coatings will hydrolyze following exposure to polar solvents (e.g., water) in vitro or in vivo.

In certain embodiments, the cured coatings and/or materials may be prepared such that they comprise one or more therapeutic agents. Such cured coatings or materials may be prepared to elute or otherwise release such therapeutic agents from the cured coatings or materials over a predetermined period of time in vivo (e.g., at least one, two, three, four, five, six, seven, fourteen, twenty-one, thirty, sixty, ninety, one hundred and twenty days or more). Examples of contemplated therapeutic agents include, but are not limited to, anti-proliferative agents, anti-inflammatory agents, antimicrobial agents, antibiotic agents and combinations thereof.

Also disclosed are methods of altering (e.g., increasing or decreasing) the hydrolysis rate of a cured or cross-linked oil coating or material by enriching or supplementing that oil with one or more alkyl-esterified fatty acids prior to curing. Such methods generally comprise the steps of enriching one or more oils (e.g., a native plant triglyceride oil) used to form the cured oil coating with one or more oil or fatty acid alkyl esters (e.g., linear or branched $C_1$-$C_6$ lower alkyl esters) thereby forming a blended or enriched oil composition. The blended or enriched oil may be exposed to curing conditions (e.g., thermal curing condition) to form the cured oil material or coating. In certain embodiments, the hydrolysis rate of such cured oil coating or material is increased relative to the coating or material formed from the un-enriched or native triglyceride oil. In other embodiments, the hydrolysis rate of such cured oil coating or material is decreased relative to the coating or material formed from the un-enriched or native triglyceride oil (e.g., such that the biocompatible coating is non-absorbable).

In an example embodiment, the cured oil based products or materials are prepared using oil blends that impart different physical characteristics (e.g., exhibit faster or slower hydrolysis rates) to such cured oil based products or materials relative to the cured native or non-enriched oil. In accordance with the present invention, suitable native or non-enriched triglyceride oils may include, but are not limited to fish oil, flaxseed oil, grapeseed oil, safflower oil, soybean oil, corn oil, olive oil and combinations thereof. In one embodiment of the present invention, the cured oil based products or materials may be prepared by enriching or supplementing the native triglyceride oil used to prepared such cured oil based product, coating or material with between about 1% and about 99% fatty acid alkyl esters prior to curing, (e.g., about 5%, about 10%, about 15%, about 20%, about 25%, about 30%, about 35%, about 40%, about 50%, about 60%, about 75%, about 80%, about 90%, about 95%, about 99% or more fatty acid alkyl esters) depending upon the desired physical characteristics of the final cured oil.

The above discussed, and many other features and attendant advantages of the present invention will become better understood by reference to the following detailed description of the invention when taken in conjunction with the accompanying examples.

DETAILED DESCRIPTION OF THE INVENTION

Figure 1:
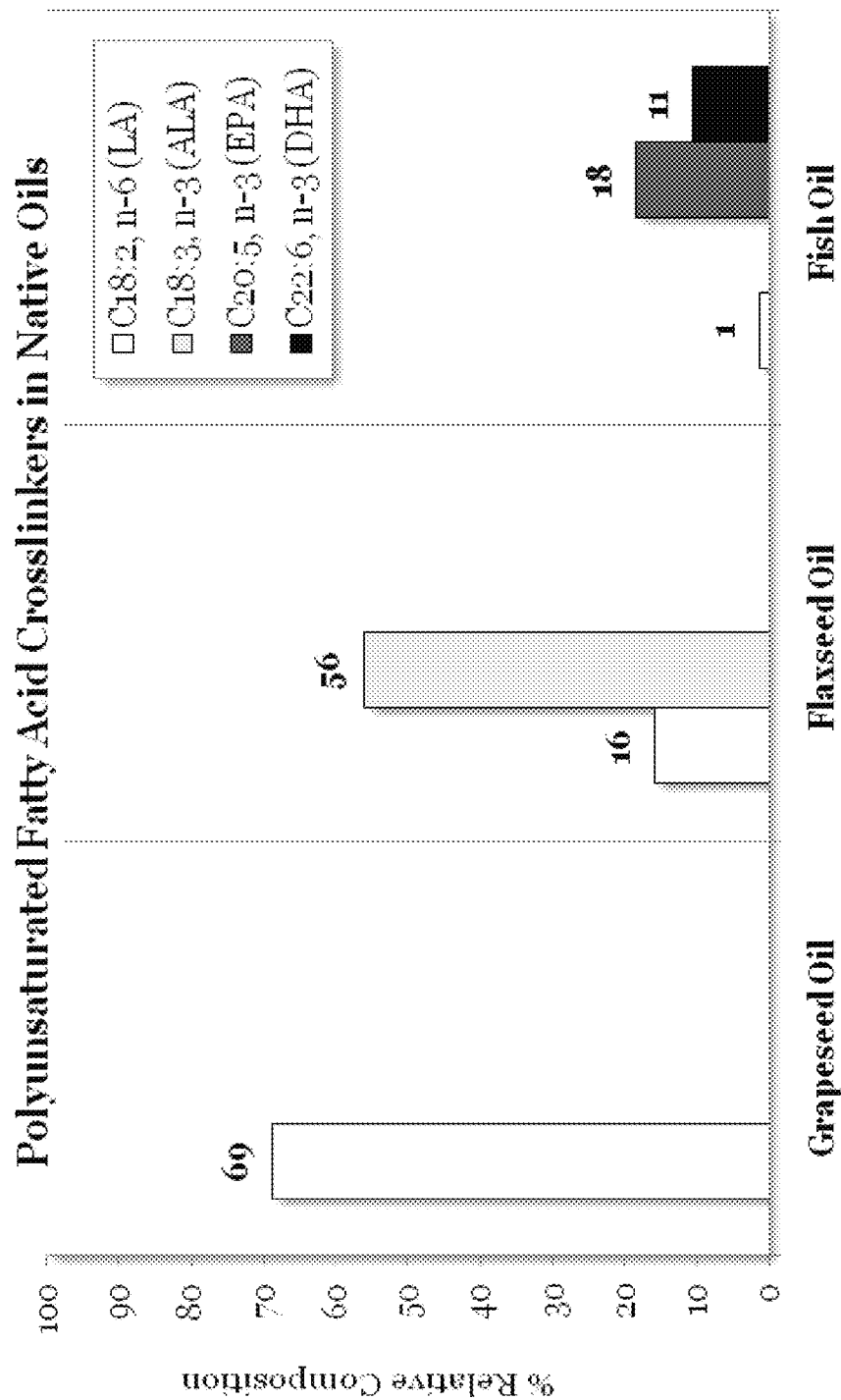
FIG. 1 illustrates the relative amounts of the polyunsaturated fatty acids linolenic acid (LA), alpha linoleic acid (ALA), eicosapentaenoic acid (EPA) and docosahexaenoic acid (DHA) present in three native triglyceride oils. As illustrated, the major polyunsaturated fatty acid species present in both grapeseed and flaxseed oils are LA and ALA, respectively. EPA and DHA are the two main polyunsaturated fatty acids present in native fish oil. The polyunsaturated fatty acids EPA, DHA, ALA and LA are responsible for the solidification observed following exposure of such native oils to thermal curing conditions.

The present invention is based on the discovery that the chemical properties of oils may be used to predict the physical properties of a resulting cured oil based product or material that is prepared therefrom, and in some instances the ability of the cured oil or material to form a biocompatible gel, material or coating, which may for example, be used as a standalone article, such as a film, particle or alternatively as coating on a medical device. The present invention is also based upon the finding that the chemical and physical properties of cured oil based products or materials that are prepared from native or non-enriched oils (e.g., properties such as the rate of hydrolysis of the cured oils in vitro or in vivo) may be modified by enriching such native or non-enriched oils with fatty acid alkyl esters prior to exposure to curing conditions. For example, in certain embodiments, the rate of hydrolysis of cured oils may be modified (e.g., increased or decreased) by blending such triglyceride oils with fatty acid alkyl ester oils prior to curing. In other embodiments, cured oil materials can be produced which are biocompatible, but are not hydrolyzable in-vivo. Additionally, the polarity as well as the cross-linked structure of cured oil materials can be altered as a means of controlling the release of therapeutic agents to a target organ or tissue.

In various embodiments, the cured oil based coatings and materials described herein are formed from or otherwise derived from oils (e.g., marine oils and/or plant oils), and in particular from the constituent fatty acids (e.g., polyunsaturated fatty acids) that comprise such oils. Generally, such fatty acids may be present in the oil in their native triglyceride form and/or as free fatty acids, fatty acid alkyl esters, monoglycerides and/or diglycerides. Also disclosed herein is the exposure of such oils to curing conditions (e.g., thermal curing conditions) such that cured or cross-linked oil based materials and/or coatings are formed. In certain embodiments, such cured or cross-linked oil based materials, and/or coatings are formed without the use of chemical cross-linking agents or additives. Such cured or cross-linked oil based materials may be used for a variety of applications.

For example, in certain embodiments a homogeneous solid cured oil material may be useful as a dissolvable barrier or a drug delivery matrix or coating (e.g., as a coating on a medical device). In other embodiments, the materials or coatings are porous (e.g., coatings on a medical device comprising one or more voids).

As used herein to qualify the oil-derived coatings, materials, gels, films, particles and any other partially solidified compositions of the present invention, the term "cured" means that the oil has been subjected or exposed to some degree of processing, for example thermal or ultraviolet light exposure, such that some degree of oxidative cross-linking (e.g., partial or complete non-polymeric cross-linking) of the constituent fatty acids present in such oils is catalyzed. Contemplated methods for curing oils (e.g., native and/or enriched oils) to produce a cured or partially-cured material or coating include, but are not limited to, heating (e.g., by employing an oven, a broadband infrared light source, a coherent infrared light source such as a laser, and combinations of the foregoing) and ultraviolet (UV) irradiation. The exposure of such oils to curing conditions (e.g., thermal curing at 200° F. in the presence of oxygen) catalyzes the oxidation of the constituent fatty acids in the oil, thereby resulting in the cross-linking of such fatty acids (i.e., oxidative cross-linking). In certain embodiments, such cross-linking of fatty acids is achieved without reliance upon external cross-linking agents. In accordance with some embodiments of the present invention, the cured oils are characterized by an increase in viscosity relative to the uncured oils.

In various embodiments, increases in viscosity observed upon curing some oils may occur as a result of the cross-linking of one or more fatty acids (e.g., fatty acid alkyl esters or fatty acid triglyceride esters) that comprise such oils. In other embodiments, increases in viscosity observed upon curing some oils may occur as a result of the volatilization of one or more species (e.g., as saturated or monounsaturated fatty acid ethyl esters or as secondary oil oxidation by-products including aldehydes, ketones, alcohols and/or hydrocarbons) present in the oil. Continued curing of the oil may increase the number or the degree of fatty acid cross-linking and thereby increase the viscosity of such cured oil material such that a solid or a semi-solid coating, material or gel is produced. In certain embodiments, such solid or semi-solid cured oil materials are suitable for use as a coating on a device (e.g., medical device).

Oils (e.g., blended oil compositions prepared by enriching native fish oil triglycerides with fish oil ethyl esters and/or various plant oil triglycerides) may be partially cured (e.g., by exposure to heat). In certain embodiments, partially curing oils induces an initial amount of fatty acid oxidative cross-linking of such fatty acids and in certain embodiments may increase the viscosity of such oils. The process of partially curing an oil has the advantage of creating an initial platform of oxidized fatty acid cross-links that are capable of being hydrolyzed by tissue in vivo (e.g., by human tissue). Accordingly, in certain embodiments, the oils are cured to induce partial cross-linking of the constituent fatty acids that comprise such oils.

It has been determined that the ability of an oil (e.g., a plant or marine oil) to undergo cross-linking is dependent upon the constituent fatty acids comprising such oil and furthermore, that the ability of an oil to cross-link may be manipulated by altering its fatty acid composition. For example, contemplated herein are modifications made to native or non-enriched oils to increase the probability that the fatty acids comprising such oils will oxidize and/or cross-link (e.g., upon exposure to curing conditions). As used herein to qualify one or more oils, the term "non-enriched" refers to an unmodified oil, whether synthetically derived or in its native or natural state. Non-enriched or native oils may include, for example, marine oil triglycerides or alkyl esters, and plant triglycerides including, but not limited to, flaxseed oil, grapeseed oil, safflower oil, soybean oil, corn oil, echium oil, hempseed oil, walnut oil, olive oil and combinations thereof. The designation "non-enriched" is intended to distinguish such oils from their enriched counterparts (e.g., blended oil compositions comprising a plant oil enriched with one or more lower alkyl fatty acid esters) which are also the subject of the present invention and in certain instances is used synonymously with the term "native."

The physical characteristics of the cured oils of the present invention are a function of the chemical characteristics of the oil from which they were prepared, and such chemical characteristics may be used to predict the physical characteristics of the cured oil composition (e.g., ability to be hydrolyzed). For example, upon exposure to curing conditions (e.g., by thermal or ultraviolet treatment), some non-enriched oils may remain in a liquid state that may be difficult to physically manipulate or that may not be physically suitable as a stable coating on a medical device, but may be suitable for other applications. As shown in Table 1 below and as further illustrated in the Examples, upon exposure of some native or non-enriched oils to thermal curing conditions for at least about 24 hours at about 200° F. the resulting cured oil materials demonstrated varying degrees of solidification and/or changes in viscosity. For example, native olive oil did not produce a solid coating and remained liquid throughout the curing process. Native corn oil and soybean oil, on the other hand, demonstrated an increase in viscosity, but did not demonstrate the physical handling characteristics seen for example with cured fish, grapeseed, safflower and flaxseed oils following exposure to the same curing conditions. Although not all oils are capable of forming cured coatings or materials, such oils or materials may be suitable for alternative uses.

TABLE 1

| Oil Type | Physical Observations |
| --- | --- |
| Fish oil | Forms solid coating |
| Olive oil | No solidification - remains completely liquid |
| Flaxseed oil | Forms solid, flexible coating |
| Grapeseed oil | Forms solid, slight tacky flexible coating |
| Soybean oil | Some solidification - very sticky |
| Safflower oil | Forms solid, slight tacky flexible coating |
| Corn oil | Very little solidification - very sticky and wet |

Figure 2A:
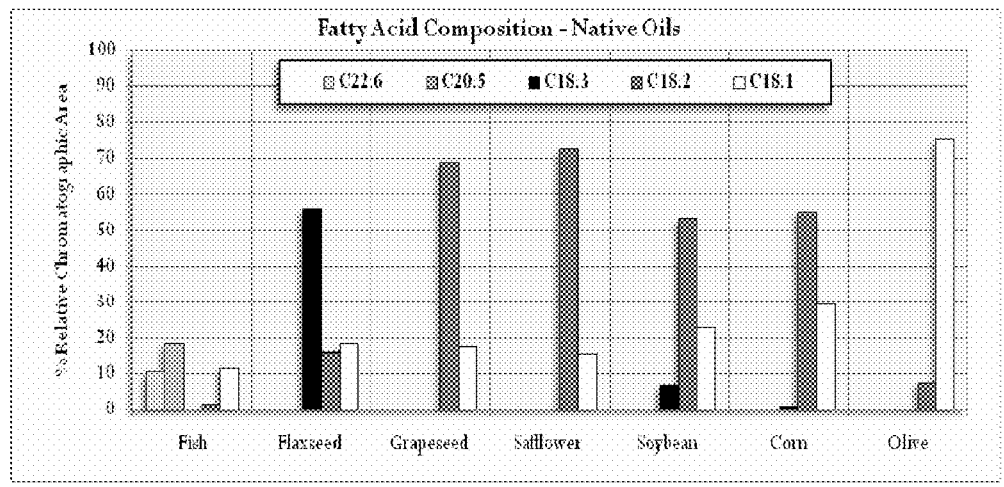
FIG. 2A illustrates the predominant poly- and monounsaturated fatty acids present in native fish oil, flaxseed oil, grapeseed oil, safflower oil, soybean oil, corn oil and olive oil.

To determine the relevant characteristics of oils that influence their ability to oxidize and/or form coatings or materials following exposure to curing conditions, the oils used to prepare such coatings or materials were evaluated to determine their constituent fatty acids and the relative concentrations of such fatty acids in such oils. The fatty acid compositions of native or non-enriched oils (e.g., marine oils and plant oils) are unique relative to each other. For example, FIG. 2A illustrates the unsaturated fatty acid compositions of non-enriched fish, flaxseed, grapeseed, safflower, soybean, corn and olive triglyceride oils as determined by gas chromatography. The fatty acid compositions of the same non-enriched oils subjected to thermal curing for 24 hours at about 200° F. are presented in FIG. 2B. By comparing the fatty acid compositions of oils both pre- and post-exposure to curing conditions and then correlating the differences to the observed physical properties of the cured coatings prepared from such oils it is possible to correlate the physical characteristics of such cured oils to such oil's chemical composition.

When correlated to the physical characteristics of the cured oils, as shown in Table 1, it was determined that curing of native or non-enriched oils and the ability (or inability) of such cured oils to form materials or coatings was directly dependent on the fatty acid composition of the oil from which such cured oils were prepared. In particular, it was discovered that the more polyunsaturated fatty acids present in the non-enriched oil, the more efficient that oil would be at undergoing oxidative cross-linking and forming a cured material, gel or coating. Specifically, the C22:6, C20:5, C18:3, and/or C18:2 polyunsaturated fatty acids present in fish and flaxseed oils are more efficient in forming a cured or cross-linked oil based material, gel or coating. Conversely, the oils which are deficient in the C22:6, C20:5 and C18:3 polyunsaturated fatty acids are more prone to forming less viscous (e.g., more liquid-like) compositions.

Figure 2B:
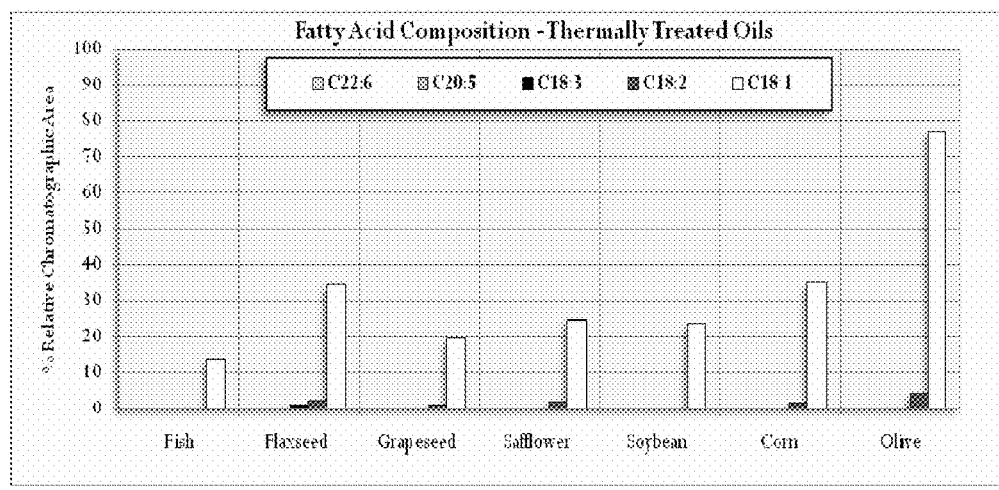
FIG. 2B illustrates the remaining poly- and monounsaturated fatty acids present in fish oil, flaxseed oil, grapeseed oil, safflower oil, soybean oil, corn oil and olive oil after exposure to thermal curing conditions.

These findings are supported by contrasting the presence of polyunsaturated fatty acids in the non-enriched oils both pre- and post-exposure to curing conditions as shown in FIGS. 2A and 2B. Upon exposure to the curing conditions (e.g., thermal curing), the polyunsaturated fatty acids present in the native or non-enriched oils are modified. While not wishing to be bound by any particular theory, it is believed that the polyunsaturated fatty acids are oxidized and participate in the formation of non-polymeric fatty acid cross-linkages that develop during exposure to curing conditions and which are characteristic of oils which form cured coatings or materials. The degree of cross-linking observed in the cured oil based materials (which is a function of the concentration and size (i.e., chain length) of polyunsaturated fatty acids present in the oil from which such cured materials was prepared) directly correlates to the viscosity of such cured material. In particular, increases in the viscosity of cured oil materials correlate to increases in intermolecular linkages or cross-links resulting from the increased concentration of available cross-linking fatty acids. Increases in viscosity are also related to the volatility of the oil and, for example, the constituent fatty acid species comprising such oil. Generally, the constituent species comprising the oil that are not participating in the cross-linking reactions described herein (e.g., saturated and monounsaturated fatty acid alkyl tails) may be fractured and the released hydrocarbon chains volatilized from the oil upon prolonged exposure to thermal curing or vacuum conditions and thereby cause an increase the viscosity of the cured oil materials prepared therefrom.

Polyunsaturated oils with only two double bonds in their fatty acid chains (e.g., non-enriched grapeseed and safflower oils which have C18:2 fatty acids) are capable of forming a semi-solid or solid composition, but only in the presence of a higher concentration of C18:2 fatty acids (e.g., more than about 65-70% C18:2 polyunsaturated fatty acids). Oils containing less polyunsaturated fatty acids (e.g., soybean and corn oils which contain less than about 60% polyunsaturated fatty acids) demonstrate an increase in viscosity following exposure to curing conditions, but remain sticky and fluid. Finally, oils that contain predominantly monounsaturated fatty acids (e.g., non-enriched olive oil) are unable to form a cured material or coating on a selected substrate (e.g., a polypropylene mesh) and remain in a liquid state following exposure to curing conditions.

The comparison of the fatty acids, and in particular, the polyunsaturated fatty acids (PUFA), present in such native or non-enriched oils both pre- and post-exposure to curing conditions reveals that certain polyunsaturated fatty acids are being consumed following exposure of such oils to thermal curing conditions, thereby confirming that such fatty acids are participating in the cross-linking reaction that is catalyzed by exposure to such thermal curing conditions. The polyunsaturated fatty acids from native fish oil triglycerides that are participating in the cross-linking reactions include the C22:6, C20:5, C18:3 and C18:2 fatty acids, as evidenced by their absence in the cured coating. In comparison, the plant oils polyunsaturated fatty acids participating in the cross-linking reactions include the C18:3 and C18:2 fatty acids, as evidenced by their absence or reduced concentration in the cured materials. The concentrations of plant oil polyunsaturated fatty acids (e.g., relative to native fish oil triglycerides) capable of participating the cross-linking reactions correlate with a reduced ability of the fatty acids present in some the subject plant oils to participate in oxidative cross-linking reactions and thereby form a solid coating or coating. Consistent with the properties observed for some of the cured plant oils (e.g., little to no solidification following exposure to thermal curing conditions), the concentrations of monounsaturated fatty acids present in the plant oils (e.g., C18:1 monounsaturated fatty acids) generally remained consistent both before and after exposure of the subject plant oils to thermal curing conditions. The lack of consumption of the C18:1 monounsaturated fatty acids therefore confirms that such monounsaturated fatty acids that are present in the plant oil triglycerides (e.g., C18:1 fatty acids) are not participating in the oxidative cross-linking reactions. Similarly, the relatively low concentrations of polyunsaturated fatty acids in some of the plant oil triglycerides (e.g., corn oil and olive oil) correlates to the inability of such plant oils to form solidified cross-linked materials, gels or coatings following exposure to thermal curing conditions.

The identification of the constituent fatty acids comprising the oils that participate in the oxidative cross-linking reactions provides valuable information that can be used to further manipulate the behavior of other oils. For example, the ability of the polyunsaturated fatty acids EPA and DHA to participate in oxidative cross-linking and form solid coatings provides information that may be used to direct the modification of other oils that do not efficiently undergo oxidative cross-linking to form solid coatings. In particular, certain oils (e.g., plant oils that are partially deficient in polyunsaturated fatty acids) may be enriched with other secondary, tertiary and/or quaternary oils known to be high in polyunsaturated fatty acids to promote cross-linking of such oils and the production of a cured oil based material or coating. Enriching oils with, for example a secondary oil, therefore provides a means of imparting one or more desired characteristics to the oil and the cured oil coating or materials prepared therefrom. Generally, enrichment may be accomplished by combining one or more secondary oils (e.g., native or synthetic marine oils) to a primary oil (e.g., a native plant oil). For example, the enrichment of oils (e.g., native fish oil triglyceride esters) with fatty acid alkyl esters (e.g., lower alkyl esters of eicosapentaenoic acid and/or docosahexaenoic acid) has been found to modify and/or enhance the physical and chemical properties of the cured oil.

As the term is used herein to qualify one or more oils, "enriched" refers to oils to which have been added one or more secondary oils. Generally, enrichment imparts one or more benefits to the oil or the cured oil material or coating prepared from such oil. In certain embodiments, the secondary oil used to enrich, for example a plant oil, comprises one or more fatty acid alkyl esters (such as, for example, ethyl esters of fish oil with concentrated levels of EPA and/or DHA). Curing of enriched oils has lead to the development of biocompatible materials and coatings demonstrating modified hydrolysis characteristics relative to the cured non-enriched oil. By varying the degree of enrichment (i.e., the concentration of fatty acid alkyl esters in the native or non-enriched oil) the properties of the cured oil can be specifically modified (e.g., the rate at which the cured oil hydrolyzes can be increased). In some embodiments, an oil is enriched with a secondary, tertiary or quaternary oil of different origin(s). For example, a plant oil (e.g., flaxseed oil triglycerides) may be enriched with a marine oil (e.g., native fish oil triglycerides) and vice versa to form a homogeneous blended oil. Such blended oils may be exposed to curing conditions to catalyze cross-linking of the constituent fatty acids (e.g., polyunsaturated fatty acids) that comprise such blended oils and thereby form a hybrid cured coating or material Enrichment of oils with fatty acid alkyl esters may be used as a means to alter the chemical and physical characteristics of oils. For example, cured oils that are resistant to in vivo hydrolysis may be considered for targeted delivery and extended or long-term release of a therapeutic agent to an intended site of action. Enrichment of such oil prior to curing may be used as a means of modifying the chemical and physical characteristics of the cured oil such that it may be easily hydrolyzed in vivo. The ability to manipulate coating hydrolysis behavior may be exploited depending on specific release requirements based on the properties of one or more therapeutic agents and the doses needed to effectuate a therapeutic response.

In certain embodiments the cured oil coating or material is hydrolyzable (e.g., in vivo). The ability of a cured coating or material to be hydrolyzable may be a function of both the types and the quantity of cross-links formed between the constituent fatty acids of the oil material following exposure to curing conditions. Accordingly, in some embodiments the cross-links or partial cross-links comprise bonds that render such coating or material hydrolyzable in vivo (e.g., ether and ester cross-links). In particular applications where the cured oil coating or material will be applied as a coating onto a device (e.g., a medical device) or used as a stand-alone film for in vivo applications, it may be preferable that the coating hydrolyzes in vivo into fatty acids, glycerols, and glycerides; hydrolyzes in vivo into non-inflammatory components; and/or contains an amount of polar hydroxyl or carboxylic acid groups sufficient to facilitate hydrolysis in vivo.

Alternatively, in one embodiment of the present invention, enrichment may also be used as a means to alter the characteristics of the cured oil such that the cured oil material is resistant to hydrolysis relative to the non-enriched oil (e.g., by blending oils). For example, an oil may be enriched or otherwise combined with a second oil such that upon exposure to curing conditions, the cured oil material, or coating is non-absorbable or is poorly absorbable in vivo, yet would still be biocompatible. In this particular embodiment, enrichment using an oil may provide a means of conferring altered chemical or physical properties to the cured oil. For example, if the intended use of the cured oil requires a less viscous cured oil composition, a second oil comprising one or more fatty acids which are less efficient in forming cross-links (e.g., C18:2 fatty acids) may be the oil used to enrich the first oil. Similarly, if the intended use of the cured oil requires that such cured oil demonstrate resistance to in vivo hydrolysis, enrichment using a second oil demonstrating such desired characteristics may be used as a means to modify the characteristics of the cured composition. Enriching a native or non-enriched oil with a second oil (i.e., blending the oils to form a homogeneous oil composition) may provide additional means of tailoring the physical and chemical characteristics of the cured material to better correlate with the intended use of such cured material.

Enrichment of oils (whether done using fatty acid alkyl esters or other triglyceride oils), and in particular the degree of enrichment, may also be used as a means of altering or manipulating the release characteristics of the cured oil as it relates to the elution of one or more therapeutic agents incorporated therein (e.g., as a coating on a drug eluting stent, hernia mesh or standalone film). For example, enrichment of an oil may be used a means of extending the release or elution of a therapeutic agent from a cured oil over extended periods of time in vivo (e.g., for delivering a therapeutic agent to its intended site of action over about 6 hours, 12 hours, 24 hours, 2 days, 3 days, 1 week, 2 weeks, 3 weeks, 4 weeks, 1 month, 2 months, 3 months, 4 months, 6 months, 9 months, 12 months or more).

Fatty acids esterified with lower alkyls such as, for example, fish oil ethyl esters are distinguishable from native oils. For example, the chemical structure of each fatty acid comprising fish oil ethyl esters is altered relative to native fish oil triglycerides such that each fatty acid ethyl ester is approximately one-third of the size of that found in native fish oil (where the fatty acids are present in triglyceride form). To distinguish the lower alkyl ester forms of fatty acids from native triglyceride fatty acids, the lower alkyl ester forms of fatty acids are generally referred to herein as "fatty acid alkyl esters". Ethyl esters of fish oil fatty acids may be referred to herein as "fish oil ethyl esters" to distinguish such ethyl esters from native fish oil triglycerides. Each fatty acid ester consists of one fatty acid linked to a lower alkyl compound (e.g., ethane) head group, while native triglyceride oils consist of three fatty acids bound to a glycerol backbone.

The fatty acid alkyl esters contemplated by the present invention include, for example, lower alkyl esters (e.g., such as methyl and ethyl esters of EPA and/or DHA). As the term is used to describe fatty acid esters, "lower alkyl" means a group having about one to about six carbon atoms in the chain, which for the purposes hereof may be straight or branched. The use of designations such as, for example, "$C_1$-$C_6$" is intended to refer to a lower alkyl (e.g., straight or branched chain and inclusive of alkenes and alkyls) having the recited range carbon atoms. Enriched oils may contain higher concentrations of esterified fatty acid species (e.g., ethyl esters of DHA and/or EPA) relative to the non-enriched oil. For example, enriched oils may contain about 5%, about 10%, about 15%, about 20%, about 25%, about 30%, about 35%, about 40%, about 50%, about 60%, about 75%, about 80%, about 90%, about 95%, about 99% or more fatty acid alkyl esters. The enrichment of fish oil (e.g., native fish oil triglycerides) with fatty acid alkyl esters can be exploited as a means to alter (e.g., increase) the hydrolysis rate of the cured oil coating. In certain embodiments, enrichment using fish oil ethyl esters (which are typically concentrated in EPA and DHA content) increase the probability (e.g., relative to the un-enriched or native oil) that the fatty acids comprising the enriched oil will cross-link and form a cured oil material or coating.

The increased rate of hydrolysis of the cured enriched oil occurs as a result of the length of the fatty acids and the availability of unsaturated sites in such fatty acids that comprise the enriched oil. Chemically, the rate of hydrolysis of the coating prepared using the enriched oil may be altered based on the selection of the esterified fatty acid. For example, factors such as the fatty acid chain length and the degree of unsaturation of the esterified fatty acid may alter the rate at which the cured enriched oil will hydrolyze.

Figure 5:
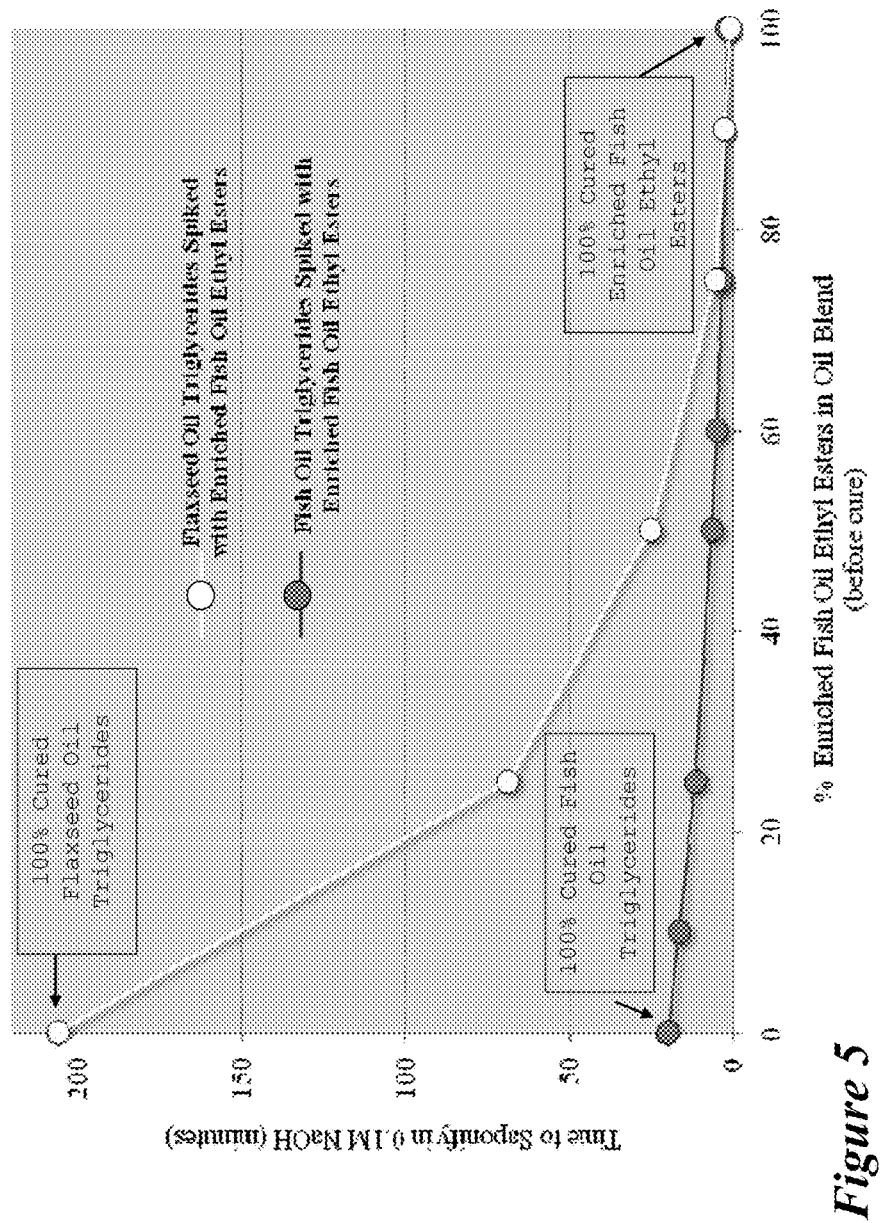
FIG. 5 illustrates the hydrolysis times in 0.1M sodium hydroxide solution of cured coatings prepared using native flaxseed and fish oils enriched with increasing concentrations of fish oil ethyl esters as a function of the ethyl ester content in such coatings. As illustrated, enrichment or "spiking" of both native fish and flaxseed oils with increasing concentrations of fish oil ethyl esters result in a corresponding reduction of the time required for the cured coatings formed from such enriched oils to hydrolyze in 0.1M sodium hydroxide solution.

The rate of hydrolysis of the cured oil is also dependent upon the nature of the fatty acids esters used to enrich the oil. For example, relative to triglyceride esters, ethyl esters of fatty acids demonstrate faster hydrolysis. Accordingly, by enriching oils with fatty acid alkyl esters (e.g., ethyl ester fatty acids) the resulting cured oil composition can be more easily hydrolyzed (i.e., the rate of hydrolysis is increased). As shown in FIG. 5, the enrichment of native fish oil triglycerides with fish oil ethyl esters was demonstrated to alter the hydrolysis rate of the cured oil coating prepared from such enriched oil. Specifically, FIG. 5 demonstrates that the kinetics of the hydrolysis rate of the cured oil coating increases as a function of enrichment with esterified fish oil fatty acids. The methods of altering the kinetics of hydrolysis of cured oils using enrichment with fatty acid alkyl esters (e.g., fish oil ethyl esters) can be applied to different oils and the hydrolysis rate can be tailored based on the oil component fatty acid chemistry and the amount of ethyl esters present, as demonstrated in FIG. 5 for flaxseed and fish oils.

In certain embodiments, the cured coatings prepared using enriched oil compositions comprise polar functional groups (e.g., hydroxyl groups) that facilitate the hydrolysis of such coating or that render such coating more hydrophilic. The presence of more polar functional groups will encourage water hydration of the cured material or coating and thereby cause such cured material or coating to hydrolyze at a faster rate. In various embodiments, enrichment (e.g., using fish oil ethyl esters) can be utilized as a means to alter (e.g., increase) the polarity of cured oil surfaces. For example, enrichment of a native plant oil with fish oil ethyl esters may be used as means of rendering the cured coating formed from such enriched oil more polar (e.g., as determined by a contact angle less than about 90°).

In various embodiments, the polarity of the cured oil materials or coatings is determined with reference to the contact angle of such cured oil material coating. Cured materials or coatings characterized as having a high contact angles (e.g., greater that 90°) indicate that such cured materials or coating are more hydrophobic in nature. Conversely, cured materials or coatings characterized has having low contract angles (e.g., less than 90°) are indicative of cured materials or coatings that are more hydrophilic in nature. In certain embodiments, the cured materials and coatings described herein have a contact angle of less than about 90° (e.g., less than about 85°, 80°, 75°, 70°, 65°, 60°, 55°, 50°, 45°, 40°, 35° or 30°).

The presence of polar functional groups in the cured materials and coatings described herein may also be determined by FTIR spectral data analysis. The FTIR spectral data analysis provides a signal plot in which functional groups present in the cured coating's molecular structure absorb at specific wavelengths. Each cured oil coating has a unique spectral profile that may be used as a fingerprint to distinguish differences in chemistry. Functional group abundance can also be inferred by absorbance intensity comparison (e.g., spectral peak height). In certain embodiments, preparing the cured materials or coatings using enriched oils increases the presence of one or more polar functional groups (e.g., increasing the presence of polar hydroxyl functional groups as determined by the coating exhibit a broad peak absorbing between 3300-3600 $cm^{-1}$).

In certain embodiments, the cured materials or coatings undergo complete hydrolysis in a basic media (e.g., 0.1M NaOH solution) in less than about 30-120 minutes (e.g., in about 30-90 minutes). In embodiments where such cured coatings or materials are used as coatings on medical devices, preferably such coatings completely hydrolyze in vivo into substantially non-inflammatory compounds (e.g., fatty acids and glycerides).

In addition to altering the rate of hydrolysis of the cured oil coating, enrichment can alter other physical properties of the cured oil. As shown in Table 2 below, the flexibility of the cured oil coating appears unaffected until an enrichment with at least 75% fish oil ethyl esters is achieved. Enrichment with a fish oil ethyl ester concentration of 75% resulted in a cured coating that became physically stiffer, which may be useful or desirous in the formation of stand alone articles, such as films, particles and stents for some alternative applications. Similarly, the cured oil formed using 100% fish oil ethyl ester oil is inelastic, which may also be useful in some alternative applications. Enrichment of native oils (e.g., using fish oil ethyl esters) therefore provides a means of modifying the physical properties of cured oil materials prepared from native oils.

TABLE 2

| % Enriched Fish Oil Ethyl Ester in Native Fish Oil Triglycerides | Physical Handling Description of Cured Coating | Time of Hydrolysis |
| --- | --- | --- |
| 0 | Uniform texture; flexible | 20 min 13 sec |
| 10 | Uniform texture; flexible | 16 min 52 sec |
| 25 | Uniform texture; flexible | 11 min 43 sec |
| 50 | Uniform texture; flexible | 6 min 30 sec |
| 60 | Uniform texture; flexible | 5 min 8 sec |
| 75 | Uniform texture; less flexible | 3 min 39 sec |
| 100 | Leaves residue on liner; rigid/will crack | 2 min 0 sec |

In certain embodiments, the cured coatings and materials described herein comprise one or more therapeutic agents. As used herein, the phrase "therapeutic agent(s)" refers to a number of different drugs or agents presently available, as well as future agents that may be beneficial for use with methods and processes described herein. The therapeutic agent can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, antimicrobial agents, anti-imaging agents, anesthetic agents, therapeutic agents, tissue absorption enhancers, anti-adhesion agents, germicides, anti-septics, analgesics, prodrugs thereof, and any additional desired therapeutic agents such as those listed in Table 3 below.

TABLE 3

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Anti-inflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |

TABLE 3-continued

| CLASS | EXAMPLES |
|---|---|
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporin, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, doxorubicin, ranpirnas, troglitzon, valsarten, pemirolast, C-MYC antisense, angiopeptin, vincristine, PCNA ribozyme, 2-chloro-deoxyadenosine, mTOR targeting compounds |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibation of Protein Synthesis/ECM formation | Halofuginone, prolyl hydroxylase inhibitors, C-proteinase inhibitors |
| Anti-infective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, triclosan, chlorhexadine selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma -1b, Interluekin - 10 |
| Immunosuppressive/Immunomodulatory Agents | Cyclosporin, rapamycin, mycophenolate motefil, leflunomide, tacrolimus, tranilast, interferon gamma-1b, mizoribine, mTOR targeting compounds |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm and that may be delivered by the cured coatings of the present invention in accordance with the methods and compositions disclosed herein include cerivastatin, cilostazol, fluvastatin, lovastatin, paclitaxel, pravastatin, rapamycin, a rapamycin carbohydrate derivative (for example, as described in U.S. Pat. No. 7,160,867), a rapamycin derivative (for example, as described in U.S. Pat. No. 6,200,985), everolimus, seco-rapamycin, seco-everolimus, and simvastatin. With systemic administration of a therapeutic agent, the therapeutic agent is administered orally or intravenously and is systemically available. However, there are drawbacks to a systemic delivery of a therapeutic agent, one of which is that the therapeutic agent travels throughout the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Calcineurin is a serine/threonine phospho-protein phosphatase and is composed of a catalytic (calcineurin A) and regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

The calcineurin signaling pathway is involved in immune response as well as apoptosis induction by glutamate excitotoxicity in neuronal cells. Low enzymatic levels of calcineurin have been associated with Alzheimers disease. In the heart or in the brain calcineurin also plays a key role in the stress response after hypoxia or ischemia.

Substances that are able to block the calcineurin signal pathway can be suitable therapeutic agents that may be administered in accordance with the methods and compositions of the present invention. Examples of such therapeutic agents include, but are not limited to, FK506, tacrolimus, cyclosporin and include derivatives, analogs, esters, prodrugs, pharmaceutically acceptably salts thereof, and conjugates thereof which have or whose metabolic products have the same mechanism of action. Further examples of cyclosporin derivatives include, but are not limited to, naturally occurring and non-natural cyclosporins prepared by total- or semi-synthetic means or by the application of modified culture techniques. The class comprising cyclosporins includes, for example, the naturally occurring Cyclosporins A through Z, as well as various non-natural cyclosporin derivatives, artificial or synthetic cyclosporin derivatives. Artificial or synthetic cyclosporins can include dihydrocyclosporins, derivatized cyclosporins, and cyclosporins in which variant amino acids are incorporated at specific positions within the peptide sequence, for example, dihydro-cyclosporin D.

In various embodiments, the therapeutic agent comprises one or more of mTOR targeting compounds and a calcineurin inhibitor. The term "mTOR targeting compound" refers to any compound that modulates mTOR directly or indirectly. In various embodiments, mTOR targeting compounds inhibit mTOR. An example of an "mTOR targeting compound" is a compound that binds to FKBP 12 to form, e.g., a complex, which in turn inhibits phosphoinostide (PI)-3 kinase, that is, mTOR. Suitable mTOR targeting compounds that may be used in accordance with the methods and processes disclosed herein include, for example, rapamycin and its derivatives, analogs, prodrugs, esters and pharmaceutically acceptable salts.

In various embodiments, the mTOR targeting compound is a rapamycin or a derivative, analog, ester, prodrug, pharmaceutically acceptably salts thereof, or conjugate thereof which has or whose metabolic products have the same mechanism of action. In various embodiments, the calcineurin inhibitor is a compound of Tacrolimus, or a derivative, analog, ester, prodrug, pharmaceutically acceptably salts thereof, or conjugate thereof which has or whose metabolic products have the same mechanism of action or a compound of Cyclosporin or a derivative, analog, ester, prodrug, pharmaceutically acceptably salts thereof, or conjugate thereof which has or whose metabolic products have the same mechanism of action.

The therapeutic agents that may be administered in accordance with the methods and compositions disclosed herein also include antimicrobial agents, including antivirals antibiotics, antifungals and antiparasitics. Specific antimicrobial agents that can be used with the cured materials and coatings of the invention include Penicillin G, Ephalothin, Ampicillin, Amoxicillin, Augmentin, Aztreonam, Imipenem, Streptomycin, Vancomycin, Clindamycin, Erythromycin, Azithromycin, Polymyxin, Bacitracin, Amphotericin, Nystatin, Rifampicin, Tetracycline, Doxycycline, Chloramphenicol, Nalidixic acid, Ciprofloxacin, Sulfanilamide, Gantrisin, Trimethoprim Isoniazid (INH), para-aminosalicylic acid (PAS), and Gentamicin.

In certain embodiments, the ability of the cured materials and coatings disclosed herein to elute one or more therapeutic agents is a function of the rate at which such cured materials or coatings ability to hydrolyze upon exposure to predetermined conditions (e.g., in vivo). Such coatings may be prepared to elute or otherwise release such therapeutic agents from the coatings over a pre-determined period of time in vivo (e.g., least one, two, three, four, five, six, seven, fourteen, twenty-one, thirty, forty, fifty, sixty, ninety, one hundred twenty days, one hundred eighty days or more). As previously discussed, the rate at which such cured materials or coatings hydrolyze may be modulated (e.g., enhanced) by modifying or enriching the oil from which such cured materials or coatings are prepared. Accordingly, in certain embodiments, enrichment (e.g., using fish oil ethyl esters) can be utilized as a means to alter (e.g., increase) the rate at which one or more therapeutic agents elutes from a cured coating or material. For example, enrichment of a native plant oil with fish oil ethyl esters may be used as means of increasing the rate at which a cured coating formed from such enriched oil hydrolyzes and therefore elutes one or more therapeutic agents. Similarly, one or more oils (e.g., native fish oil) may be enriched with a secondary oil (e.g., flaxseed oil) to retard the rate at which a coating formed from such enriched oil hydrolyzes and one or more therapeutic agents elute.

While certain compounds and methods of the present invention have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

EXAMPLES

The following examples illustrate that the chemical properties of oils, and in particular of the constituent fatty acids that comprise both marine oils and plant oils, may be used to predict the ability of such oils to undergo oxidative cross-linking, for example upon exposure to thermal curing conditions. Additionally, the physical properties of the coatings or materials prepared upon exposure of such oils to, for example, thermal curing conditions may also be predicted based on the chemical properties of the oil. These teachings provide means of manipulating oils such that cured coatings or materials prepared therefrom have one or more properties capable of rendering such coatings or materials fit for a particular purpose (e.g., as a drug-eluting coating on a medical device).

Example 1

The purpose of the present experiments was to investigate the ability of native or "un-enriched" plant oils to thermally cross-link and form a cured oil material or coating; to compare the properties of such plant oils to native fish oil triglycerides; and to investigate how the fatty acid composition of the plant oils evaluated influenced the properties and chemistry of the final cured oil coatings prepared therefrom. The plant oils investigated included corn oil, echium oil, flaxseed oil, grapeseed oil, hempseed oil, olive oil, peanut oil, safflower oil, soybean oil, sunflower oil and walnut oil.

The oils were each gravimetrically applied to a 6×6 cm polypropylene mesh by pipette and subsequently thermally cured by exposure to 93° C. for a minimum of 24 hours. After thermal exposure, the coated mesh samples were physically inspected for oil solidification, appearance and texture. As depicted in Table 1, following the exposure of specific plant oils to thermal curing conditions, varying degrees of solidification were observed. For example, some of the plant oils evaluated (e.g., olive oil) did not cure or cross-link and remained in a liquid state. Other oils appeared to exhibit an increase in viscosity and partially solidified around the polypropylene mesh, but subsequent heat exposure did not result in the formation of a solid, dry coating. Some of the plant oils investigated readily cross-linked and formed a continuous coating around the polypropylene mesh following exposure to thermal curing conditions. In particular, cured coatings physically similar to the coatings prepared using native fish oil triglycerides were achieved with flaxseed, safflower and grapeseed oils.

By evaluating the fatty acid compositions of native oils and comparing such fatty acid compositions to the fatty acid compositions of cured coatings prepared from such oils, it was determined that the fatty acid composition of the subject oils was the determining property responsible for the physical differences observed in the thermally-cured plant oils. The plant oils that were capable of cross-linking to form a cured material or coating upon exposure to thermal conditions contained higher concentrations of the polyunsaturated $C_{18}$ fatty acids.

FIG. 1 graphically illustrates and compares the typical concentrations of the major polyunsaturated fatty acid constituents found in grapeseed oil, flaxseed oil and fish oil that are available to participate in the oxidative cross-linking reactions and are responsible for the observed formation of a solidified coating or material on or around the polypropylene mesh substrate. As illustrated in FIG. 1, the major polyunsaturated fatty acids present in both grapeseed and flaxseed oils are linolenic (LA) and alpha linoleic acids (ALA), respectively. Conversely, and as also illustrated in FIG. 1, eicosapentaenoic acid (EPA) and docosahexaenoic acids (DHA) were the two main long-chained omega-3 polyunsaturated fatty acids present in native fish oil triglycerides that were responsible for the observed solidification (i.e., ability to cross-link) following exposure of such native fish oil triglycerides to thermal curing conditions.

None of the plant oils evaluated contain EPA or DHA in their triglyceride structures. Rather, each of the plant oils evaluated comprised triglyceride molecules with unique fatty acid compositions that differed markedly from the fatty acids found in fish oil. For example, the alkyl tails of the fatty acids components of the plant oil triglycerides ranged from about $C_{16}$-$C_{18}$ in length with varying degrees of saturation (e.g., each unsaturated fatty acid in the evaluated plant oils contained one to a maximum of three double bonds). In contrast, the alkyl tails of the fatty acid components of the fish oil triglycerides ranged from about $C_{14}$-$C_{22}$ in length with varying degrees of saturation (e.g., each unsaturated fatty acid contained one to a maximum of six double bonds).

The native fish oil triglycerides and the selected non-enriched plant oils were also analyzed to determine the relative amounts of the constituent fatty acids that comprise such oils. The amount of constituent fatty acids present in the oils were then compared to the fatty acid composition of the thermally cured coatings that were prepared using the native fish oil triglycerides and plant oils. As illustrated in FIG. 2A, the fish oil triglycerides predominantly consist of polyunsaturated fatty acids that are capable of participating in the oxidative cross-linking reactions described herein (e.g., C22:6, C20:5, C18:3 and C18:2 fatty acids). Following their exposure to thermal curing conditions, the polyunsaturated fatty acids present in the fish oil (e.g., the C22:6, C20:5, C18:3 and C18:2 fatty acids) participated in the oxidative cross-linking reaction and were consumed, as evidenced by their absence in the cured coating. Therefore, the consumption of polyunsaturated fatty acids such as, for example, EPA and DHA, that are present in the fish oil triglycerides following exposure to thermal curing conditions confirms that such polyunsaturated fatty acids are participating in the thermally-induced oxidative cross-linking reaction and the formation of the cross-linked material or coating.

Compared to native fish oil, the plant oils evaluated predominantly have C18:2 polyunsaturated fatty acids and C18:1 monounsaturated fatty acids. FIG. 2A further illustrates the absence or relatively low concentration of, for example, the C22:6, C20:5 and C18:3 polyunsaturated fatty acids in the plant oils evaluated. The comparatively low concentrations of polyunsaturated fatty acids (e.g., relative to native fish oil triglycerides) correlates with a reduced ability of the fatty acids present in some the subject plant oils to participate in oxidative cross-linking reactions and thereby form a solid coating or material. Consistent with the properties observed for some of the cured plant oils (e.g., little to no solidification following exposure to thermal curing conditions) and as depicted in FIGS. 2A and 2B, the concentrations of monounsaturated fatty acids present in the plant oils (e.g., C18:1 monounsaturated fatty acids) generally remained consistent both before and after exposure of the subject plant oils to thermal curing conditions. The lack of consumption of the C18:1 monounsaturated therefore confirms that the monounsaturated fatty acids present in the plant oil triglycerides (e.g., C18:1 fatty acids) are not participating in the oxidative cross-linking reactions. Similarly, the relatively low concentrations of polyunsaturated fatty acids in some of the plant oil triglycerides (e.g., corn oil and olive oil) correlates to the inability of such plant oils to form solidified cross-linked materials or coatings following exposure to thermal curing conditions.

Example 2

As an alternative to native fish oil which comprises fatty acids largely in triglyceride form, fish oil fatty acids in ethyl ester form were evaluated for their ability to undergo oxidative cross-linking and form solid coatings upon exposure to thermal curing conditions. To distinguish the ethyl ester forms of such fish oil fatty acids from native fish oil in triglyceride form, the ethyl ester forms of fish oil fatty acids are referred to herein as the "fish oil ethyl esters".

The fish oil ethyl esters evaluated were distinguishable from the native fish oil in several ways. For example, the chemical structure of each fatty acid comprising the fish oil ethyl esters was altered relative to native fish oil such that each fatty acid molecule was approximately one-third of the size of that found in native fish oil where the fatty acids are largely present in triglyceride form. Furthermore, each fatty acid comprising the fish oil ethyl esters consisted of one fatty acid linked to an ethanol head group, while native triglyceride oils consist of three fatty acids connected via a glycerol backbone.

The fatty acid composition of the fish oil ethyl esters also differed from that of native fish oil. For example, the fish oil ethyl esters contained the same polyunsaturated fatty acid species as the native fish oil, however such polyunsaturated fatty acids were present in different proportions. The higher concentrations of EPA and DHA present in the fish oil ethyl esters corresponds to approximately twice the amount of omega-3 polyunsaturated fatty acids EPA and DHA found in native fish oil, which typically contains about 16-18% EPA and 10-11% DHA.

To evaluate the ability of the fish oil ethyl esters to undergo oxidative cross-linking and form coatings, the fish oil ethyl esters were applied gravimetrically to 6×6 cm polypropylene mesh by pipette and subsequently cured for 24 hours at 200° F. For comparison purposes, native fish oil was also applied gravimetrically to 6×6 cm polypropylene mesh by pipette and subsequently cured for 24 hours at 200° F.

A dry, solid, coating was formed upon exposure of the fish oil ethyl esters to the thermal curing conditions. Small voids were also observed within the gaps of the polypropylene mesh substrate onto which the fish oil ethyl ester coating was formed, that were not observed on the coatings formed using the native fish oil triglycerides. The voids were evident despite having applied the same mass of starting oil per unit of polypropylene mesh surface area. The presence of such voids in the coatings were attributed to the higher volatility of the fish oil ethyl esters and the volatilization of fatty acids that were not directly participating in the oxidative cross-linking reactions during the exposure of such fish oil ethyl esters to thermal curing conditions (e.g., saturated and monounsaturated fatty acids).

The cured coatings made from the fish oil ethyl esters were observed to be physically stiffer (i.e., more rigid and less flexible) and more inelastic in texture when compared to the coatings prepared using native fish oil under the same conditions. The increased physical rigidity observed with the coating prepared using the fish oil ethyl esters was likely due to increased intermolecular linkages or cross-links resulting from the increased concentration of available cross-linking fatty acids (e.g., EPA and DHA).

Figure 3:
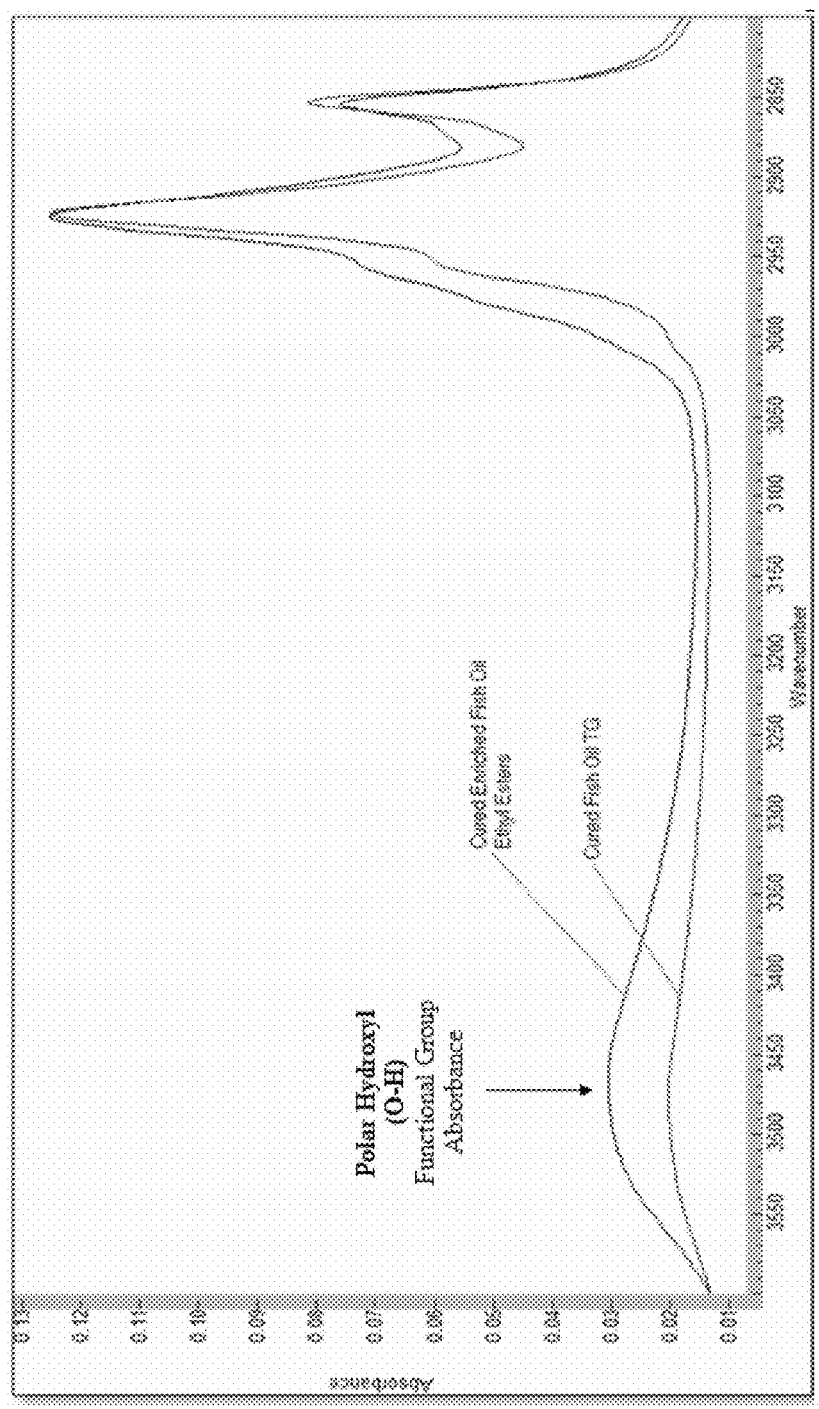
FIG. 3 illustrates FTIR spectral identity analysis indicating that the coating prepared using the fish oil ethyl esters had significantly increased hydroxyl functional group substitution relative to the coating prepared using native fish oil triglycerides. The increased hydroxyl functional groups present in the coating prepared using the fish oil ethyl esters contribute to that coating's hydrophilicity and its ability to uptake water and subsequently hydrolyze at a more rapid rate.
Figure 4:
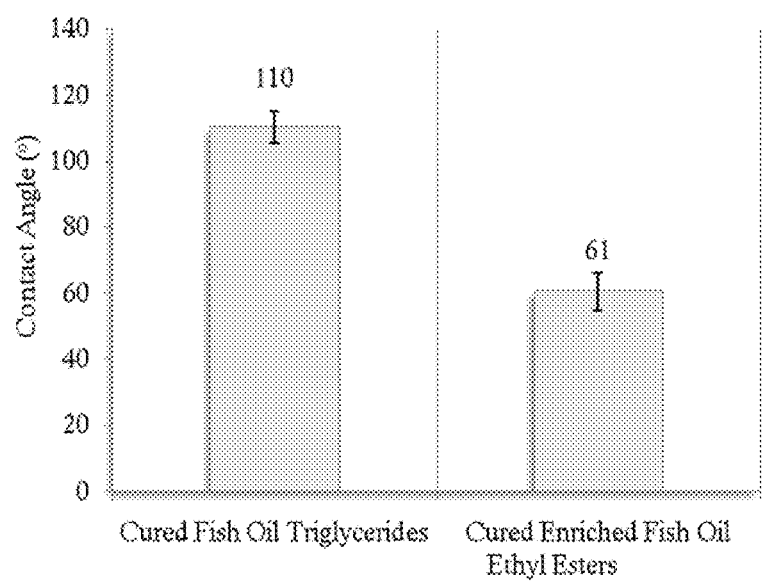
FIG. 4 depicts a comparison of a contact angle analysis of coatings prepared using fish oil ethyl esters and coatings prepared using native fish oil triglycerides. As illustrated, the coating prepared using the fish oil ethyl esters had a significantly lower contact angle, demonstrating that the coating was much more hydrophilic in nature relative to the coatings prepared using native fish oil triglycerides.

Further evaluation of the coatings prepared using fish oil ethyl esters also revealed marked differences in the chemical and physical properties of such coatings compared to the coatings prepared using native fish oil triglycerides. In vitro bench hydrolysis testing was performed using an aqueous 0.1 molar sodium hydroxide (0.1M NaOH) solution and demonstrated that the coatings prepared from the fish oil ethyl esters dissolved at a much faster rate than the coatings prepared using native fish oil triglycerides. As illustrated in FIG. 3 FTIR spectral identity analysis indicated that the coatings prepared using the fish oil ethyl esters had significantly increased hydroxyl functional group substitution, which would contribute to the coating's ability to uptake water and subsequently hydrolyze at a more rapid rate. Contact angle analysis also demonstrated that the coatings prepared using fish oil ethyl esters were much more hydrophilic in nature compared to the coatings prepared using native fish oil triglycerides. For example, as illustrated in FIG. 4, the coatings prepared using the fish oil ethyl esters had a significantly lower contact angle relative to the coatings prepared using native fish oil. The combination of this FTIR spectral data and contact angle measurements demonstrate that the coatings and materials prepared using fish oil ethyl esters appeared to be more polar and hydrophilic relative to the coatings prepared using native fish oil triglycerides. The enhanced polarity and hydrophilicity of such coatings enhance the hydration of the coatings, thereby causing such coatings to hydrolyze at a faster rate.

Example 3

Blends of native oils from different origins (e.g., plant oils and fish oils) and fatty acid compositions were investigated to determine means of manipulating the physical properties of the oils and of the cured coatings prepared using such oils. Native fish oil triglycerides were enriched with oils of plant origin at various ratios to form a blended oil composition and such blended oils were evaluated to determine their ability to cross-link and form solidified coatings or materials upon exposure the thermal curing conditions. Additionally, further studies were conducted using blended oils that were prepared by enriching native fish oil triglycerides with fish oil ethyl esters. In the foregoing studies, the blended oil formulations were prepared gravimetrically at different ratios (e.g., at 10%, 25%, 50%, 75%, and/or 90% w/w), were each applied as homogenous liquids onto 6×6 cm Prolite Ultra polypropylene mesh by pipette and subsequently exposed to thermal curing conditions for at least 24 hours at 200° F. Following their exposure to thermal curing conditions, the coated meshes were further evaluated.

Blends of Native Plant and Fish Oils

Blended oils were prepared by enriching native plant-oils with native fish oils to determine if the polyunsaturated fatty acids from native fish oil (e.g., EPA and DHA) would participate in the oxidative cross-linking reactions with the polyunsaturated fatty acids from plant oils (e.g., LA and ALA) to form cured hybrid coatings or materials. The plant oils assessed included flaxseed oil, which (as discussed in Example 1) was capable of forming a solid coating or material upon exposure to thermal curing conditions, and olive oil, which (as also discussed in Example 1) was incapable of forming a solid coating and remained liquid during exposure to thermal curing conditions.

Following exposure to thermal curing conditions, the blended combination of native fish oil and flaxseed oil readily formed homogenous coatings at all of the ratios evaluated. In particular, upon exposure to thermal curing conditions, polyunsaturated fatty acids from the native fish oil triglycerides (e.g., EPA and/or DHA) participated in an oxidative cross-linking reaction with polyunsaturated fatty acids from flaxseed oil triglycerides (e.g., LA and/or ALA) and thereby formed coatings on the polypropylene mesh. The observed solid coatings produced upon thermal curing of the blended fish oil and flaxseed oil combinations support the conclusion that fatty acids of different origins (e.g., plant- and marine-based polyunsaturated fatty acids) can readily cross-link with each other to form solid coatings and materials.

To determine whether enrichment of olive oil with native fish oil triglycerides could facilitate the cross linking of the fatty acids present in olive oil, additional studies were conducted using a blended oil formulation prepared by gravimetrically combining native fish oil and olive oil at different ratios. Following exposure to thermal curing conditions, the blended oil combinations of native fish oil and olive oil did not produce a solid homogeneous coating at any of the ratios evaluated. Accordingly, enrichment of olive oil with fish oil triglycerides could not induce cross-linking of the polyunsaturated fatty acids present in the olive oil with the polyunsaturated fatty acids present in the native fish oil triglycerides to form a homogeneous solid coating or material.

Blends of Native Fish Oil Triglycerides and Fish Oil Ethyl Esters

Additional studies were conducted to determine whether fatty acids from different triglyceride oils would react to form a cross-linked network with the fish oil ethyl ester fatty acids having an enriched EPA and DHA content. Blended oil formulations were prepared by enriching native fish oil or flaxseed oil with fish oil ethyl esters at various ratios.

Following exposure of the blended oils to thermal curing conditions, all of such blended oil combinations at all ratios evaluated produced solid homogeneous coatings on the polypropylene mesh substrates to which they were applied. Upon exposure to thermal curing conditions, the fish oil triglycerides enriched with the fish oil ethyl esters produced homogenous, coatings at all ratios evaluated. Similarly, the flaxseed oil enriched with fish oil ethyl esters produced homogenous, coatings at all ratios evaluated. The foregoing provides evidence that blended oil combinations can be used to produce coatings or materials and that triglyceride fatty acids can react with ethyl ester fatty acids to form oxidative cross-links.

Example 4

Additional studies were conducted to evaluate and compare the ability of coatings prepared using plant oils, marine oils, fish oil ethyl esters and blended oil combinations of the foregoing, to hydrolyze in an alkaline hydrolysis solution. In the foregoing studies, the oil formulations were prepared and applied as homogenous liquids onto 6×6 cm polypropylene mesh by pipette and subsequently exposed to thermal curing conditions for at least 24 hours at 200° F. Samples were obtained by taking a 1×1" laser-cut area of each cured oil coated mesh. Such samples were then placed in clear glass vials, submerged into a fixed volume of 0.1 molar sodium hydroxide solution and monitored for complete coating dissolution. During the coating hydration and hydrolysis reaction time, the vials were heated to 37° C. and stored on a shaker table rotating at approximately 75 rotations per minute. The temperature evaluated was equivalent to the typical body temperature to which the coating on a substrate (e.g., a medical device) would be exposed in vivo. The purpose of the present studies was to provide a metric with which to compare coating integrity and resilience under basic conditions. The data generated with this in vitro hydrolysis test method are useful to help predict coating breakdown and performance in vivo.

Under the test conditions evaluated, the coatings prepared using native fish oil triglycerides completely hydrolyzed into solution after about 20-30 minutes. All of the plant oil coatings evaluated, which included flaxseed, safflower and grapeseed oils, took significantly longer to hydrate, hydrolyze and dissolve. In comparison, the coatings prepared using the fish oil ethyl esters hydrolyzed at a significantly faster rate.

Coatings were also prepared using blends of either native fish or plant oil triglycerides enriched with fish oil ethyl esters and were also evaluated for ability to be hydrolyzed upon exposure to the basic media. The coatings prepared using the blended oils comprised either native fish oil or flaxseed oil enriched with fish oil ethyl esters provided unique, altered hydrolysis profiles. A graph depicting these in vitro hydrolysis times for these oil blends as a function of ethyl ester quantity in the blended oil material is illustrated in FIG. 5. Similarly, Table 2 illustrates that the direct relationship between the concentrations of fish oil ethyl esters and hydrolysis time. Specifically, the time of hydrolysis of the cured oil coatings can be increased by increasing amount of fish oil ethyl esters used to enrich the native fish oil used to prepare such coatings.

As depicted in FIG. 5, as the concentration of fish oil ethyl ester in the blended oil formulation was increased, the final cured coating produced had a reduced hydrolysis time in the 0.1M NaOH solution. Therefore, the present studies provide that enrichment of native plant or marine oils with fish oil ethyl esters can be utilized to alter the hydrolysis properties of coatings prepared using such native fish oils or plant oils.

Example 5

Figure 6:
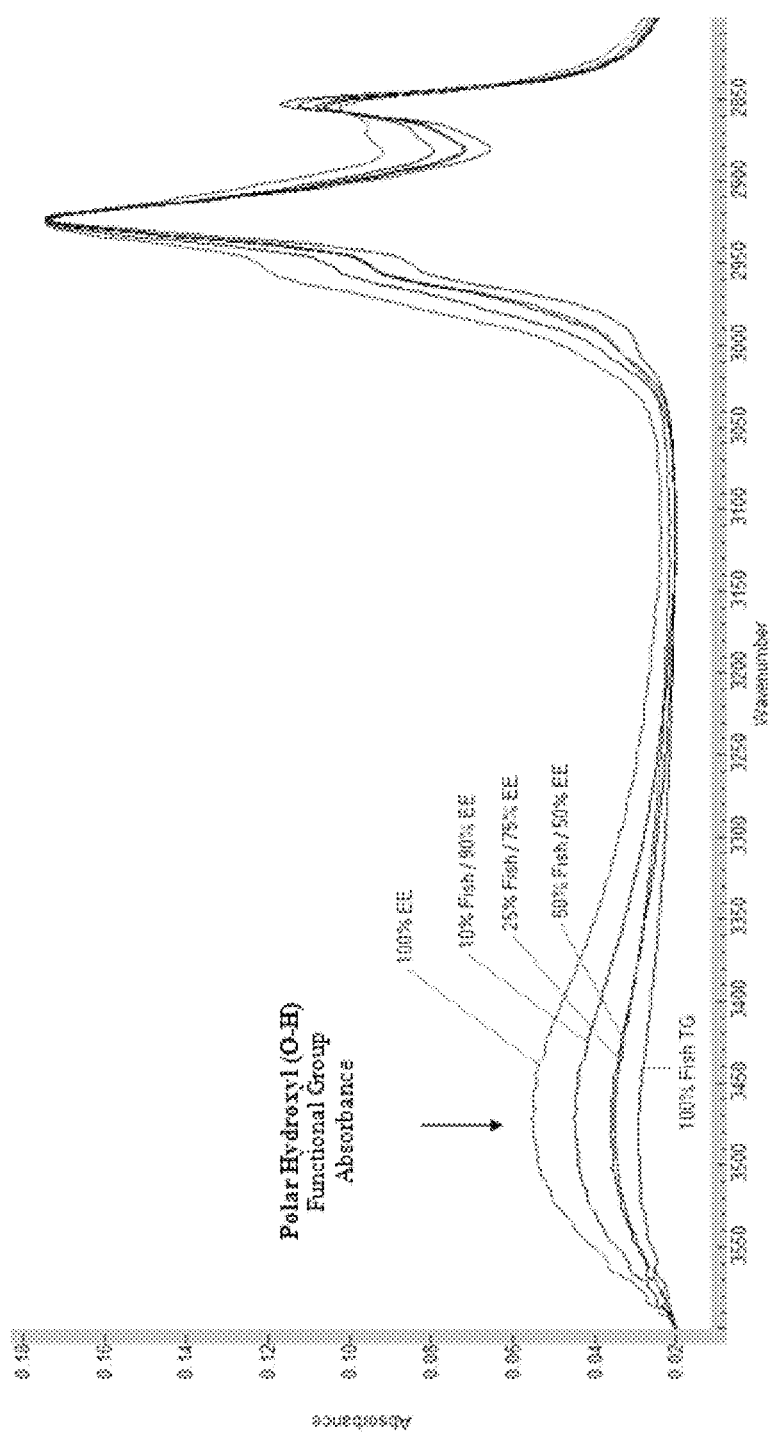
FIG. 6 depicts the overlaid FTIR spectral identity analysis of various coatings prepared using various blended concentrations of native fish oil triglycerides enriched with fish oil ethyl esters. Increases in the concentration of fish oil ethyl esters in the blended oil cause a corresponding increase in the absorbance intensity corresponding to polar hydroxyl functional groups absorbing between 3300-3600 $cm^{-1}$.
Figure 7:
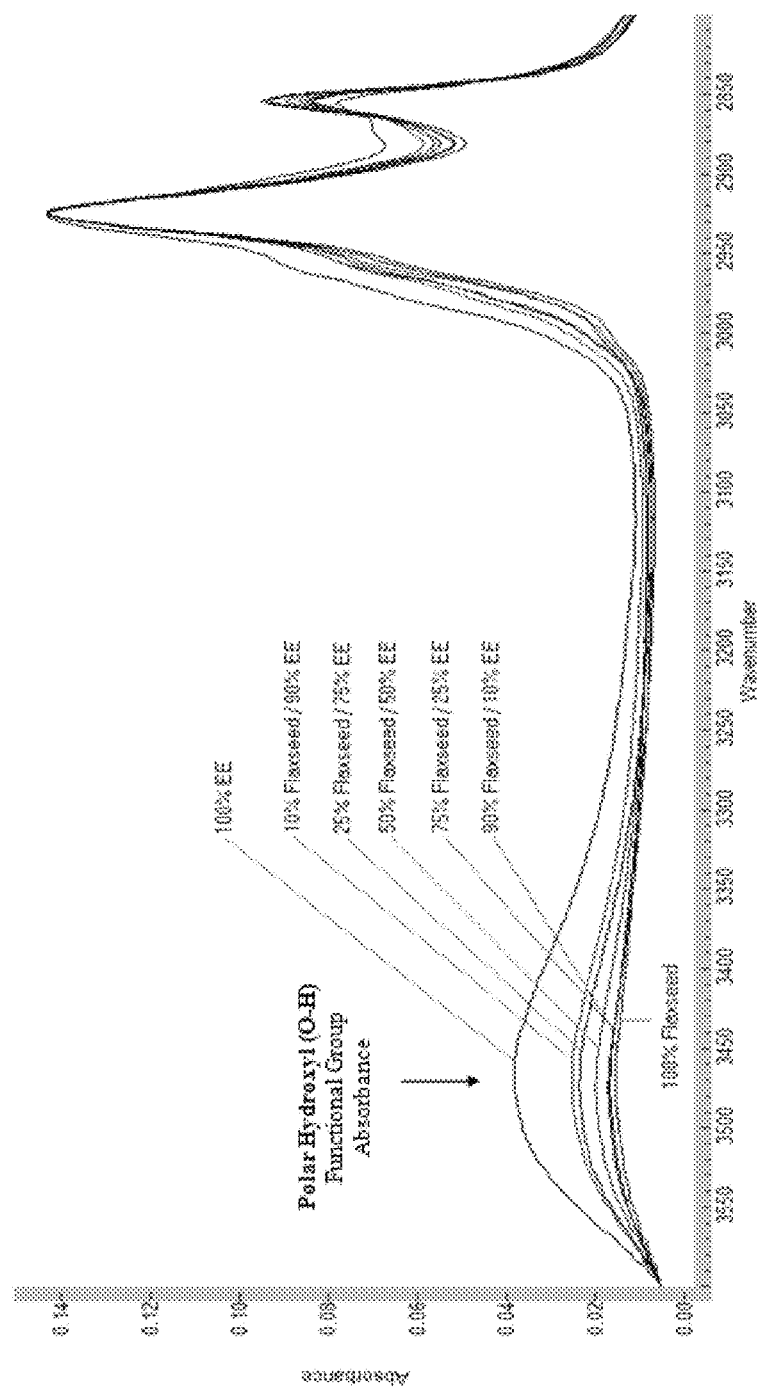
FIG. 7 illustrates the overlaid FTIR spectral identity analysis of various coatings prepared using various blended concentrations of native flaxseed oil triglycerides enriched with fish oil ethyl esters. Increases in the concentration of fish oil ethyl esters in the blended oil cause a corresponding increase in the absorbance intensity corresponding to polar hydroxyl functional groups absorbing between 3300-3600 $cm^{-1}$.

The coatings prepared using the blended oil formulations (i.e., plant oil or fish oil enriched with fish oil ethyl esters) were also evaluated for coating polarity using FTIR spectral identity and surface contact angle analysis. The FTIR spectral identity provides a signal plot in which functional groups present in the coating's molecular structure absorb at specific wavelengths. Each cured oil coating prepared had a unique spectral profile that may be used as a fingerprint to distinguish differences in the chemical structure of such coating. For example, the presence of hydroxyl functional groups in the coating exhibited a broad peak absorbing between about 3300-3600 cm$^{-1}$. As depicted in FIG. 6 and FIG. 7, a direct relationship was observed between the amount of fish oil ethyl esters added to the native fish oil or plant oil and the absorbance of the final cured coatings by FTIR due to hydroxyl group abundance.

Figure 8:
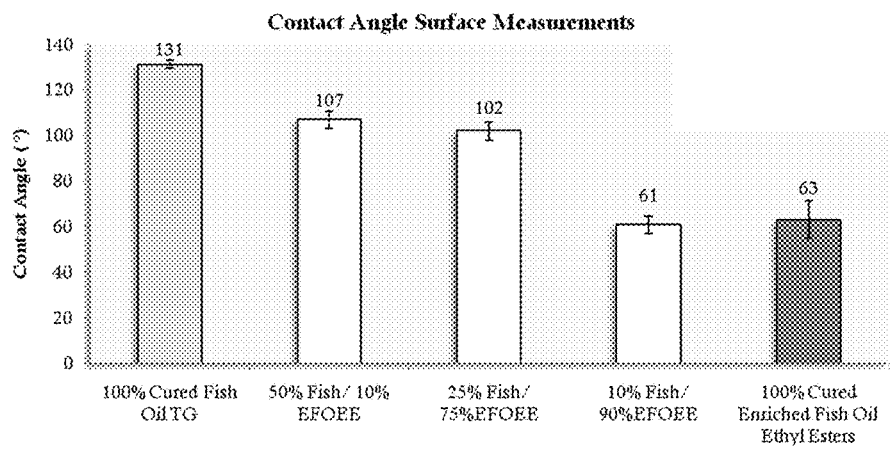
FIG. 8 graphically depicts contact angle measurements recorded from various coatings prepared using blends of native fish oil triglycerides enriched with fish oil ethyl esters at various ratios. Increases in the concentration of the fish oil ethyl esters in the blended starting oil composition resulted in lower contact angles of the cured coatings prepared from such blended oil compositions, thus indicating that the surface of such coatings are more hydrophilic.
Figure 9:
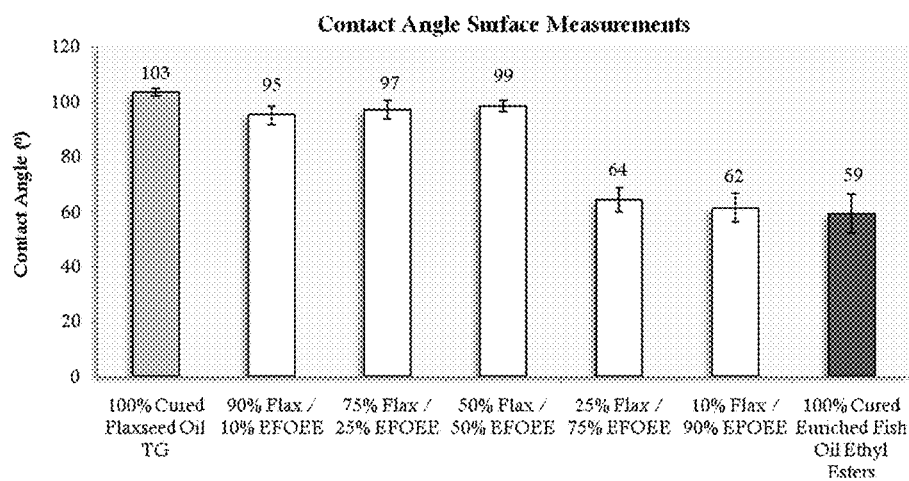
FIG. 9 graphically illustrates contact angle measurements recorded from various coatings prepared using blends of native flaxseed oil triglycerides enriched with fish oil ethyl esters at various ratios. Increases in the concentration of the fish oil ethyl esters in the blended oil composition generally resulted in lower contact angles of the coatings prepared from such blended oil compositions, thus indicating that the surface of such coatings are more hydrophilic.
Figure 10:
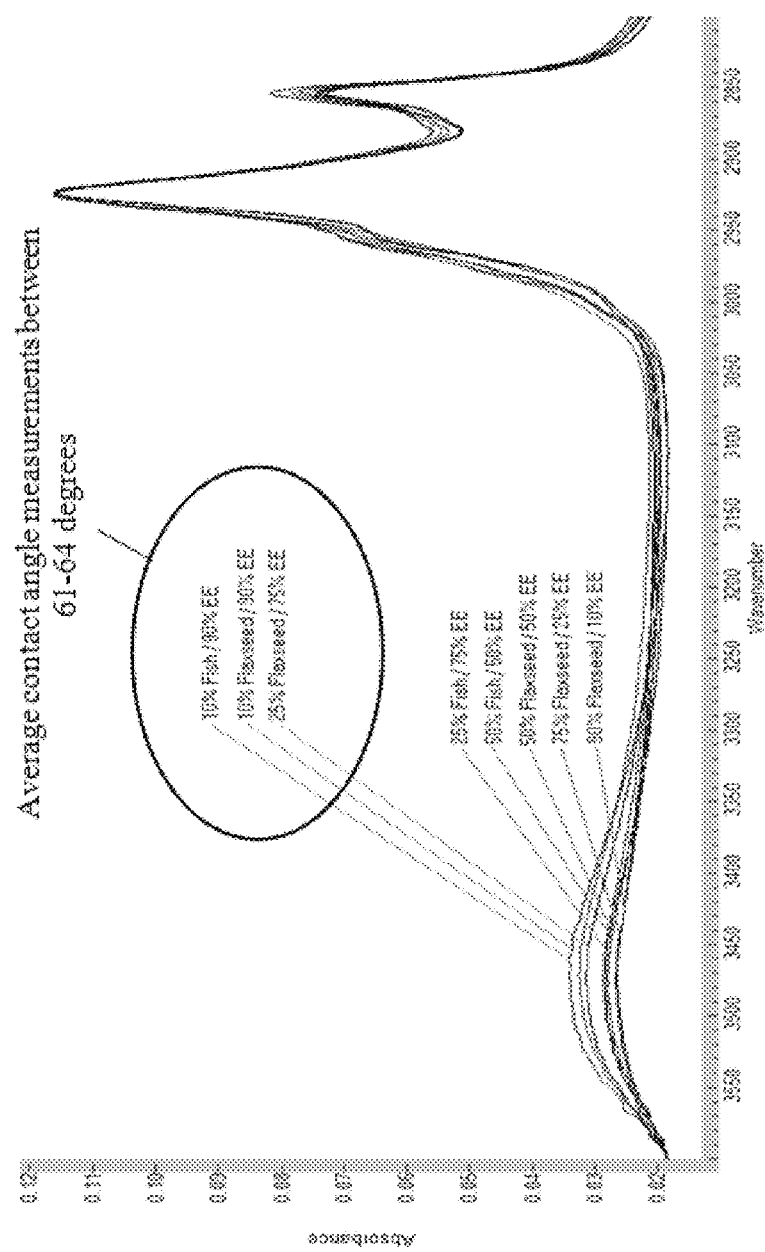
FIG. 10 represents overlaid FTIR spectral profiles of the blended cured coatings prepared using native fish oil or flaxseed oil triglycerides enriched with fish oil ethyl esters. Blended oils that produced coatings having the lowest contact angle measurements are identified. Increases in the concentration of the fish oil ethyl esters in such flaxseed oil based blended compositions in excess of 75% and in excess of 90% in the native fish oil resulted in average contact angle measurements between 61-64°.

The polarity and the hydrophilicity of the coatings prepared using blended oils were also evaluated and compared by determining the contact angles of such coatings. The contact angle analysis was conducted by placing a drop of water onto the coating and thereafter a snapshot image was immediately acquired. The image of the water droplet upon the surface of the coating was then analyzed to calculate the angle at which the water droplet contacted the surface of the coating. Angles of higher degree (e.g., greater than 90°) indicate that the surface is more hydrophobic in nature. Conversely, angles of a lower degree (e.g., less than 90°) indicate that the surface is more hydrophilic in nature. The presence of polar species on the surface chemistry of a solid material encourages wettability (i.e. hydrophilicity). As depicted in FIGS. 8 and 9, the surface contact angle analysis demonstrated that the blended coatings prepared from fish oil or plant oils that were enriched with higher concentrations of fish oil ethyl esters produced more polar coatings. Accordingly, there is a direct relationship between the amount of fish oil ethyl esters in the blended oil composition and the rate of hydrolysis of the cured oil coating prepared therefrom, further supporting the conclusion that the physical properties (e.g., in vitro hydrolysis) of the cured oil coating or material can be manipulated by increasing amount of fatty acid ethyl esters added to both plant and marine oils. As the amount of fish oil ethyl esters in the starting oil formulations was increased, the final cured coatings exhibited increased absorbance by FTIR due to hydroxyl group abundance that correlated with the observed contact angles, as depicted in FIG. 10.

The FTIR spectral data and contact angle measurements presented herein demonstrate that the addition of fish oil ethyl esters can be utilized to alter the polarity of cured oil coatings or materials. The ability to modify the surface chemistries of cured oil coatings and materials can be advantageous in that more polar functional groups will encourage water hydration and thereby facilitate the hydrolysis of the coating.

Example 6

The instant studies were conducted to compare the release profiles of a model therapeutic compound from the coatings prepared using native plant oils or fish oils enriched with ethyl ester fatty acids. Three cross-linked oil coatings were prepared by applying native fish oil, flaxseed oil or fish oil ethyl esters to 6×6 cm polypropylene mesh by pipette and subsequently curing for 24 hours at 200° F. Triclosan, a lipophilic, hydrophobic, antimicrobial therapeutic agent, was incorporated into the three different oil formulations at the same target drug load. Samples of each cured coating prepared were then subjected to a drug dissolution testing. High performance liquid chromatography (HPLC) was performed to assay the dissolution aliquots of the quantity of drug eluted from the coatings in order to generate the release curves unique to each coating.

Figure 11:
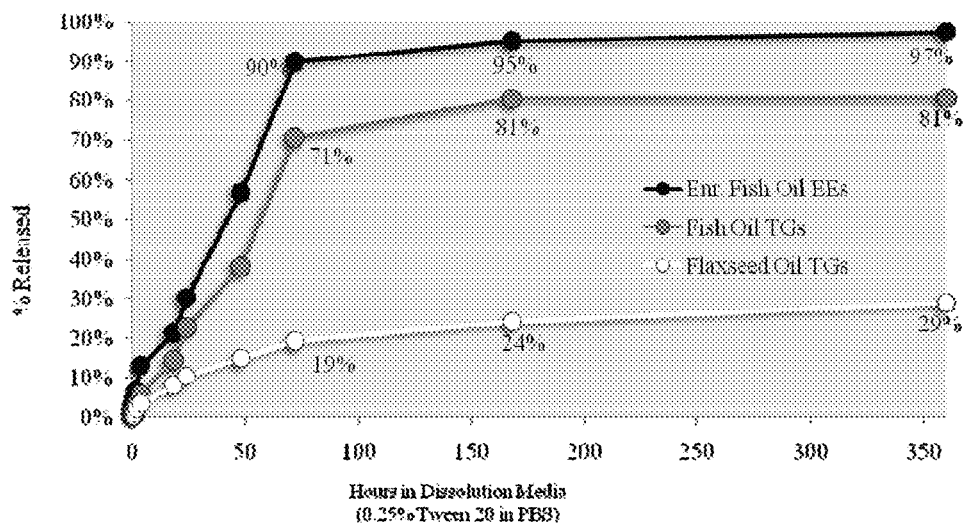
FIG. 11 illustrates dissolution curves of the therapeutic agent triclosan from coatings that were prepared using native fish oil, flaxseed oil and fish oil ethyl esters from an aqueous media. The triclosan was eluted into the aqueous dissolution media at different rates from each of the coatings into which it was incorporated. The triclosan eluted from the coating prepared using fish oil ethyl esters the fastest and nearly all triclosan was recovered after 3 days. The triclosan eluted from the coating prepared using native flaxseed oil triglycerides at the slowest rate as only about 30% of the triclosan was recovered from the aqueous media after 15 days.

The triclosan dissolution curves are shown in FIG. 11. Triclosan was eluted into the aqueous dissolution media (0.25% Tween 20 in PBS) at different rates, depending on the cross-linked oil coating into which it was incorporated. The coating which eluted triclosan at the fastest rate was the coating prepared using the fish oil ethyl esters. As illustrated in FIG. 11 nearly all of the triclosan was recovered from the coating prepared using the fish oil ethyl esters after 3 days. The coating which eluted triclosan at the slowest rate was the coating prepared with flaxseed oil triglycerides. As shown in FIG. 11, only about 30% of the triclosan was recovered from the coating prepared using flaxseed oil after 15 days. The present study demonstrates the ability of manipulating release of therapeutic agents from cured oil coatings of varying fatty acid composition and polarity.

Example 7

The present studies were conducted to evaluate the in vivo biocompatibility and resorption kinetics of blended coatings on polypropylene mesh. The coated polypropylene meshes were implanted into the muscle tissue of rabbit models. The cross-linked oil coatings were prepared using either native fish oil triglycerides, fish oil ethyl esters, flaxseed oil, or various blends of marine oils enriched with fish oil ethyl esters. After 2 months implantation time, the coated polypropylene meshes were harvested from the muscle tissue and evaluated microscopically.

Figure 13:
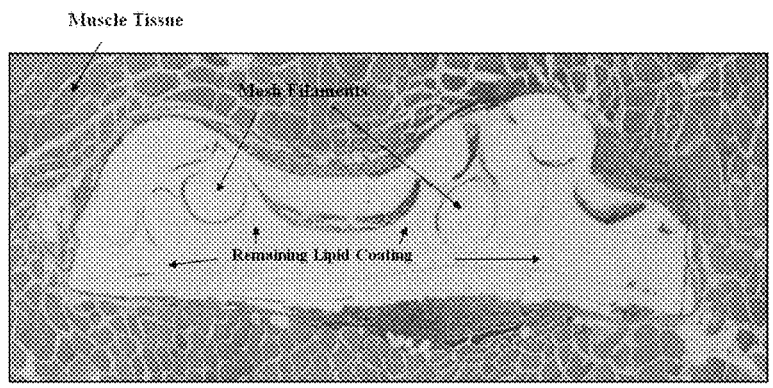
FIG. 13 depicts images of cross-sections of a coated polypropylene mesh that was prepared using flaxseed oil after two months of being implanted into rabbit muscle tissue. As illustrated, after two months of implantation in the rabbit muscle tissue, the coating did not show evidence of significant resorption.
Figure 14:
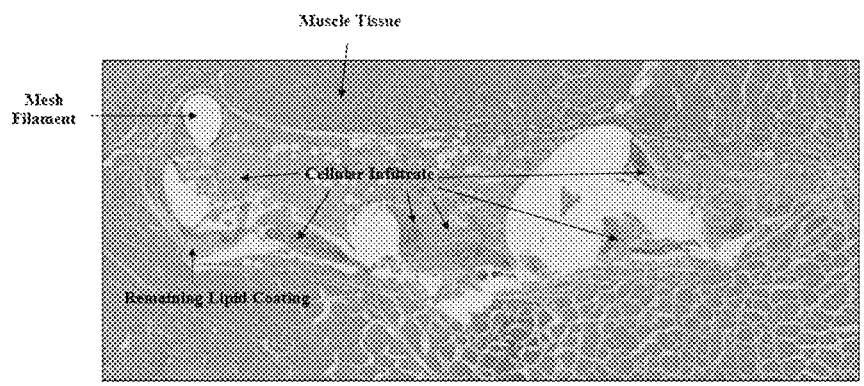
FIG. 14 depicts images of cross-sections of a coated polypropylene mesh that was prepared using a fish oil ethyl ester blended oil composition two months after being implanted into rabbit muscle tissue. As illustrated, after two months of implantation in the rabbit muscle tissue, the coating appeared to have been almost completely absorbed by the surrounding tissue.

All animals evaluated survived until scheduled sacrifice. Histological evaluation of the harvested tissue did not indicate any adverse cellular responses or inflammation with respect to any of the implant coated meshes. Microscopic evaluation of the explanted coated meshes did indicate differences in amounts of remaining coating present on the mesh as well as cellular infiltration. Images of cross-sections of the devices inserted into tissue after 2 months are shown in FIGS. 12, 13 and 14.

Figure 12:
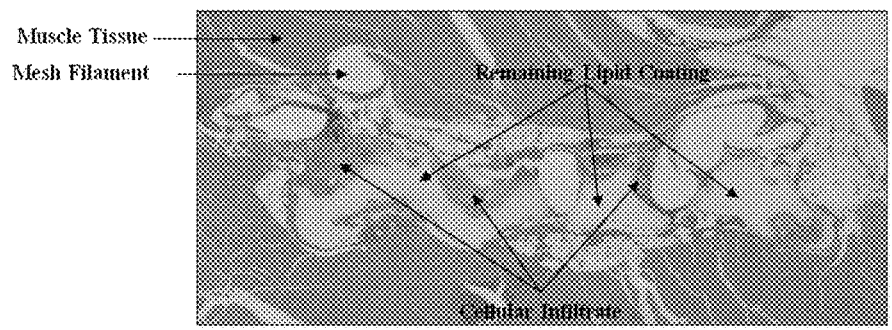
FIG. 12 depicts images of cross-sections of a coated polypropylene mesh that was prepared using native fish oil two months after being implanted into rabbit muscle tissue. As illustrated, after two months of implantation in the rabbit muscle tissue, the coating appeared to be partially absorbed by the surrounding tissue.

As illustrated in FIG. 12, after two months implantation in rabbit muscle the coating prepared using native fish oil triglycerides was partially absorbed. As illustrated in FIG. 13, the coatings prepared using flaxseed oil (which does not contain EPA or DHA) did not absorb within the two month period and appeared very similar to initial implantation. The coating prepared using blends of native fish oil and fish oil ethyl esters, however, were almost completely absorbed within the 2 month timeframe, as illustrated in FIG. 14. These differences further demonstrate that it is possible to manipulate and alter coating resorption kinetics in vivo by altering the composition of the starting oil.

Discussion

The foregoing studies illustrate that cured lipid or oil-based coatings or materials having desired properties may be formed by altering the oil composition used to prepare such cured coatings. In particular, manipulating the underlying chemical properties (e.g., fatty acid composition) of the oils (e.g., by blending with other oils) prior to exposure to, for example, thermal curing conditions, facilitates the tailoring of the cured coating's or material's physical characteristics, which include, for example polarity, flexibility and the ability to hydrolyze. Furthermore, the present inventions provide means of controlling the elution of therapeutic agents from a coating or material to thereby control the release of such therapeutic agents. The teachings provided herein also provide means of tailoring the properties of cured coatings or materials and thereby expand the potential application of oils and such cured coatings or materials prepared from such oils and thereby expand the purposes for which such oils or cured coatings may be used (e.g., as a drug-eluting coating on medical devices), and further provide that modifying the composition of starting oils provides a means of manipulating coating resorption kinetics in vivo. Accordingly, by manipulating chemical properties of oils, the compositions and methods disclosed herein effectively increase the population of available native or enriched oils that may be cured or cross-linked as well as the number of specific applications for which such oils may be used.

What is claimed is:

1. A method of increasing the in vivo hydrolysis rate of a cured oil coating having cross-linked fatty acids, wherein the method comprises the steps of (i) enriching one or more oils used to form the cured oil coating by adding one or more fatty acid ethyl esters to form an enriched oil, wherein the enriched oil comprises about 75% w/w or more of the one or more fatty acid ethyl esters, and wherein the enriched oil comprises at least 50% w/w polyunsaturated fatty acids and (ii) exposing the enriched oil to curing conditions to form the cured oil coating so that a number of polar hydroxyl functional groups are formed in the cured oil coating during curing that increases the polarity of the cured oil coating compared to what is formed during curing when the one or more oils are cured without the enriching step, thereby increasing the in vivo hydrolysis rate of the cured oil coating and providing the coating with a contact angle of less than 90°.

2. The method of claim 1, wherein the fatty acid ethyl esters comprise an ethyl ester of eicosapentaenoic acid (EPA).

3. The method of claim 1, wherein the fatty acid ethyl esters comprise an ethyl ester of docosahexaenoic acid (DHA).

4. The method of claim 1, wherein the fatty acid ethyl esters comprise ethyl esters of eicosapentaenoic acid (EPA) and docosahexaenoic acid (DHA).

5. The method of claim 1, wherein the one or more oils are selected from the group consisting of fish oil, flaxseed oil, grapeseed oil, safflower oil, soybean oil, corn oil, echium oil, hempseed oil, walnut oil, olive oil and combinations thereof.

6. The method of claim 1, wherein the enriched oil comprises flaxseed oil and ethyl esters of eicosapentaenoic acid (EPA) and docosahexaenoic acid (DHA).

7. The method of claim 6, wherein the enriched oil comprises about 10% or more w/w flaxseed oil.

8. The method of claim 1, wherein the one or more oils are marine oils.

9. The method of claim 1, wherein the enriched oil comprises fish oil and ethyl esters of eicosapentaenoic acid (EPA) and docosahexaenoic acid (DHA).

10. The method of claim 1, wherein the enriched oil comprises about 10% or more w/w fish oil.

11. The method of claim 1, wherein the enriched oil comprises at least 60% polyunsaturated fatty acids.

12. The method of claim 1, wherein the coating has a contact angle of less than 70°.

13. The method of claim 1, wherein the coating completely hydrolyzes in vivo in less than about 60 days.

14. The method of claim 1, wherein the coating completely hydrolyzes in vivo in less than about 90 days.

15. The method of claim 1, wherein the coating completely hydrolyzes in vivo into substantially non-inflammatory compounds.

16. The method of claim 1, wherein the coating has one or more polar hydroxyl groups as indicated by an infrared absorption spectrum having a peak at approximately 3300-3600 $cm^{-1}$.

17. The method of claim 1, wherein the coating further comprises one or more therapeutic agents.

18. The method of claim 17, wherein the one or more therapeutic agents are selected from the group consisting of an anti-proliferative agent, an anti-inflammatory agent, an antimicrobial agent, an antibiotic agent and combinations thereof.

19. The method of claim 17, wherein the one or more therapeutic agents are eluted from the coating over an extended period of time.

20. The method of claim 19, wherein the extended period of time is at least seven days.

21. The method of claim 19, wherein the extended period of time is at least fourteen days.

22. The method of claim 19, wherein the extended period of time is at least about thirty days.

23. The method of claim 19, wherein the extended period of time is at least sixty days.

24. The method of claim 1, wherein the curing conditions comprise heat.

25. The method of claim 1, wherein the cured oil coating forms a coating on a medical device.

26. A method of increasing the in vivo hydrolysis rate of a cured oil coating having cross-linked fatty acids, wherein the method comprises the steps of:

enriching one or more oils used to form the cured oil coating by blending in one or more fatty acid alkyl esters to form an enriched oil, wherein the enriched oil comprises about 75% w/w or more of the one or more fatty acid alkyl esters, and exposing the enriched oil to curing conditions to form the cured oil coating so that a number of polar hydroxyl functional groups are formed in the cured oil coating during curing that increases the polarity of the cured oil coating compared to what is formed during curing when the one or more oils are cured without the enriching step, thereby increasing the in vivo hydrolysis rate of the cured oil coating, wherein the coating has a contact angle of less than 90° and wherein the coating has substantially more polar hydroxyl groups than a coating formed by exposing non-enriched forms of the one or more oils to the curing conditions as indicated by an infrared absorption spectrum having a broad substantial peak at approximately 3300-3600 $cm^1$.

27. The method of claim 26, wherein the fatty acid alkyl esters comprise lower alkyl esters of fatty acids, wherein the lower alkyl esters of fatty acids are selected from the group consisting of a linear C1-C6 alkyl ester and a branched C1-C6 alkyl ester.

28. The method of claim 26, wherein the fatty acid alkyl esters are ethyl esters of fatty acids.

29. The method of claim 26, wherein the alkyl esters of fatty acids are selected from the group consisting of a linear C1-C22 alkyl ester and a branched C1-C22 alkyl ester.

30. A method of increasing the in vivo hydrolysis rate of a cured oil coating having cross-linked fatty acids, wherein the method comprises the steps of (i) enriching one or more oils used to form the cured oil coating by adding one or more fatty acid ethyl esters to form an enriched oil, wherein the enriched oil comprises about 50% w/w or more of the one or more fatty acid ethyl esters, and wherein the enriched oil comprises at least 50% w/w polyunsaturated fatty acids and (ii) exposing the enriched oil to curing conditions to form the cured oil coating so that a number of polar hydroxyl functional groups are formed in the cured oil coating during curing that increases the polarity of the cured oil coating compared to what is formed during curing when the one or more oils are cured without the enriching step, thereby increasing the in vivo hydrolysis rate of the cured oil coating.

* * * * *